(12) United States Patent
Witten

(10) Patent No.: US 7,124,044 B2
(45) Date of Patent: Oct. 17, 2006

(54) METHOD FOR RECONSTRUCTING COMPLEX WAVE ATTRIBUTES FROM LIMITED VIEW MEASUREMENTS

(76) Inventor: Alan Witten, 3308 River Walk Ct., Norman, OK (US) 73072

( * ) Notice: Subject to any disclaimer, the term of this patent is extended or adjusted under 35 U.S.C. 154(b) by 0 days.

(21) Appl. No.: 10/790,301

(22) Filed: Mar. 1, 2004

(65) Prior Publication Data
US 2005/0027769 A1 Feb. 3, 2005

Related U.S. Application Data

(60) Provisional application No. 60/490,458, filed on Jul. 28, 2003.

(51) Int. Cl.
*G06F 19/00* (2006.01)
(52) U.S. Cl. .......................... 702/77; 342/22
(58) Field of Classification Search ............... None
See application file for complete search history.

(56) References Cited

OTHER PUBLICATIONS

Search Report issued Mar. 15, 2006 for International Application PCT/US04/24058, filed Jul. 28, 2004.
Written Opinion issued Mar. 15, 2006 for International Application PCT/US04/24058, filed Jul. 28, 2004.

*Primary Examiner*—Patrick J. Assouad
(74) *Attorney, Agent, or Firm*—Fulbright & Jaworski L.L.P.

(57) ABSTRACT

A method is disclosed for reconstructing complex wave attributes from limited view measurements of a scattering object. The method involves the analytic continuation of the Fourier transform of the object function into the area in which there is an absence of K-space coverage by requiring objects to be an even function. (It is assumed that physical objects are even functions, and it is this assumption that allows analytic continuation.) When the object function is not centered at the origin, the measurements are shifted to the origin prior to determining the analytic continuation and returned to their original location following analytic continuation.

20 Claims, 34 Drawing Sheets

(a) (b)

METHOD FOR RECONSTRUCTING COMPLEX WAVE ATTRIBUTES FROM LIMITED VIEW MEASUREMENTS

PRIORITY INFORMATION

The present application claims the benefit of U.S. Provisional Application 60/490,458 filed on Jul. 28, 2003.

FIELD OF THE INVENTION

The present invention relates to the reconstruction of complex wave attributes from limited view measurements of a scattering object.

BACKGROUND

The phrase "wave based measurement" refers to the measurement of the nature of a wave at a receiver from a wave created by a source. Wave based measurements have many applications, some of which are as simple as measuring the distance from a source to a receiver. Such simple measurements are based on a measurement of the time the wave travels and, knowing the speed at which the wave travels (i.e., propagates), the distance is computed as the product of the known wave speed and the elapsed travel time.

Simple wave-based measurements, such as the one mentioned above, require that the wave travel through a homogeneous medium, i.e., that the material through which the wave travels have a uniform wave speed. When a wave travels through a medium where the wave speed (or other attributes) is not constant, the character of the recorded wave is altered. While this complication makes it impossible to use simple wave-based measurements to determine distant, it offers the possibility of applying more sophisticated analyses to characterize the medium. Such techniques are in regular use for diagnostic medicine, non-destructive evaluation (NDE), and geophysics.

What makes these applications so powerful is that changes in wave propagation characteristics are diagnostics for more fundamental material properties. For example, ultrasound has many uses in diagnostic medicine and one such use is the detection of tumors in the breast. Tumors have a density that is typically greater than healthy soft tissue, and this density difference change the propagation of high frequency acoustic waves. Similarly, differences in material properties are exploited in wave-based NDE to identify impurities or micro-fractures, and are used in geophysics to identify buried man-made objects or geologic structures such as minerals, oil, or natural gas deposits.

In most wave-based applications, the full extent of the information that is encoded in the data is not recovered. Typically, there are several material properties that alter the propagation of waves and, when considered individually, these properties serve to more completely characterize objects such as tumors. With electromagnetic waves, changes in wave character result from changes in both dielectric and electrical conductivity. Having access to each of these properties separately, rather than as a composite response, better serves to characterize the material of interest, such as distinguishing plastic from metal and wood, etc. Attenuation is a property that causes a loss of wave energy and, with electromagnetic waves, electrical conductivity causes wave attenuation. In low frequency acoustics (seismics), attenuation can be indicative of the presence of certain types of materials, most notably hydrocarbons, so that the capacity to isolate the contribution of attenuation in wave propagation can be considered a direct indicator of hydrocarbons.

It is currently possible to separate fundamental material properties from wave-based measurements. However, this capability is limited to very specific measurement configurations where there is a certain type of measurement symmetry. One example is where arrays of both sources and receivers are distributed around the circumference of a ring. A ray path is defined to be a direction of wave propagation from a source to receiver. When considering a source on one side of the ring and a receiver on the opposite side, it is clear that, within this array geometry, other sources and receivers can be paired so as to measure ray paths both opposite and perpendicular to the path of interest. A second example of symmetric geometry is an array of sources positioned along one line and an array of receivers distributed over a parallel line some distance away. Sources and receivers can be paired such that for every ray path taken to be downward from left to right, a similar ray path can be captured that is upward from left to right.

There are many other measurement configurations where this symmetry does not exist and for which there has been no way of separately extracting fundamental material properties. (Such configurations are referred to as limited view configurations.) Returning to the example regarding the detection of breast tumors discussed above, while it may be possible to completely surround some portion of the breast with a ring of ultrasonic transducers, there are portions of the breast as well as other areas of the body, such as heart, liver, kidneys, etc., that cannot be non-invasively accessed in this manner and, thus, measurements must be with limited views. Another limited view geometry is reflection where both sources and receivers are typically distributed over the same or adjacent lines. Reflection geometries are common in medical ultrasound (obstetrics, for example) and many geophysical applications such ground penetrating radar and seismic reflection (a mainstay of resource exploration).

What is needed is a methodology that will allow the isolation of individual material properties from limited view measurements. Such a methodology will have broad applications in many types of wave-based measurements.

SUMMARY OF INVENTION

The present invention may be used for acquiring data on measurement surfaces r where r is, for example, (1) arbitrary, (2) rings, spheres, or cylinders, (3) parallel or perpendicular lines, or (4) lines or curved surfaces having arbitrary orientation to each other. Measurements can be made in the time domain where the data is temporally Fourier transformed or in the frequency domain. Sources can be impulsive or continuous wave sources, and sources and receivers can have arbitrary beam patterns.

For imaging methods, the analytic continuation is applied after the data is spatially and temporally (when acquired in the time domain) Fourier transformed. This analytic continuation can be directly applied to imaging procedures that are based on Fourier transforms, such as filtered backpropagation. For imaging methods that are not Fourier transform-based, such as linear algebraic methods, the image can be first formed, spatially Fourier transformed, analytically continued, and then inverse transformed. The analytic continuation procedure given herein will properly separate real and imaginary parts of a complex set of basic material properties defined as $O=O_R+iO_I$. In the absence of analytic continuation, the shape of the object can be well defined by $|O|=\sqrt{O_R^2+O_I^2}$; however, any information about the individual contrasts, $O_R$ and $O_I$, is lost. A way to reconstruct a good shape and recover contrast is to use image 101 with or without analytic continuation to create an accurate object shape and then assign values given by $O_R$ and $O_I$ derived from analytic continuation within this shape to separately assign accurate contrasts.

With regard to reconstituting the data, the analytic continuation procedure described herein does not require imaging of separate fundamental material properties. Analytic continuation can be applied and then an image reconstructed of basic material properties. Alternatively, the data can be analytically continued and then inverse transformed to produce individual data sets for each basic property. (This procedure is referred to herein as reconstituting the data.) Also, some measurement geometries, such as rings, do lend themselves to spatial Fourier transforms. In such geometries, the data can be propagated onto lines prior to Fourier transforming.

The analytic continuation will not work directly when objects are not centered at the origin. It is, therefore, necessary to phase shift the Fourier transformed data to the origin prior to the application of the analytic continuation. After this application, an opposite phase shift is applied to restore objects to their proper position. There are several methods for phase shifting, including: (1) Identify the center of isolated objects by, for example, reconstructing $|O|$ as discussed above. This requires that acquired data be segregated into pieces, where each data segment contains information about a single object. (2) Mirroring can be applied to the data, as discussed in conjunction with FIGS. 31 and 32, such that the entire data set can be simultaneously phase shifted without the complication of isolating contributions from individual objects.

The present invention has numerous applications, including: (1) Using the analytic continuation procedure with electromagnetic waves to separately image or isolate dielectric and electrical conductivity. (2) Using the analytic continuation procedure with acoustic (seismic) waves to separately image or isolate wave speed and attenuation. (3) Using the analytic continuation procedure with acoustic (seismic) waves to separately image or isolate density, compressibility, and attenuation. (Acoustic wave speed is a composite of density and compressibility, and there are methods that exist to separately image these properties provided that wave speed information is not blended with attenuation.) (4) Using the analytic continuation procedure with electromagnetic or acoustic seismic waves on any of the many above mentioned measurement configurations and data acquisition procedures to separate basic material properties in diagnostic medicine, non-destructive evaluation, and geophysics.

A method is disclosed for reconstructing complex wave attributes described by an object function O from limited view measurements u of a measurement surface r with associated wavevector K, the method comprising the steps of processing the limited view measurements u to obtain Fourier transformed measurements ũ, determining a Fourier transformed object function Õ of the object function O, determining an analytic relationship between the Fourier transformed object function Õ and the Fourier transformed measurements ũ, analytically extending the Fourier transform Õ by specifying that Õ(K)=Õ(-K), thereby obtaining an analytically extended Fourier transform of Õ, and reconstructing the complex wave attributes by inverting the analytically extended Fourier transform of Õ.

In one embodiment, the complex wave attributes are wave speed and attenuation. In another embodiment, the complex wave attributes are dielectric and electrical conductivity. In a further embodiment, the complex wave attributes are acoustic wave speed density and compressibility.

In one embodiment, the object function is one-dimensional. In another embodiment, the object function is two-dimensional. In yet another embodiment, the object function is three-dimensional.

In one embodiment, the measurement surface r comprises a ring. In another embodiment, the measurement surface r comprises a sphere. In a further embodiment, the measurement surface r comprises a cylinder. In an additional embodiment, the measurement surface r comprises a plurality of parallel lines. In yet another embodiment, the measurement surface r comprises a plurality of perpendicular lines. In a further embodiment, the measurement surface r comprises a line and a curved surface.

In one embodiment, the limited view measurements are time domain measurements. In a further embodiment, the limited view measurements are frequency domain measurements.

Also disclosed is a method for reconstructing complex wave attributes described by an object function O from limited view measurements u of an object with associated wavevector K, the method comprising the steps of processing the measurements u to obtain Fourier transformed measurements ũ, determining a midpoint of the object, creating shifted Fourier transformed measurements $ũ_R$ by shifting the Fourier transformed measurements ũ so that the midpoint is located at the origin, determining an analytic relationship between the object function O and the shifted Fourier transformed measurements $ũ_R$, determining the Fourier transform Õ of the object function O from the Fourier transformed measurements $ũ_R$ using the analytic relationship, analytically extending the Fourier transform Õ by specifying that Õ(K)=Õ(-K), thereby obtaining an analytically extended Fourier transform of Õ, determining shifted complex wave attributes by inverting the analytically extended Fourier transform of Õ, and reconstructing the complex wave attributes by shifting the shifted complex wave attributes back to the midpoint.

In one embodiment, the step of determining a midpoint comprises the steps of determining the complex contrast of said object, determining the magnitude of the complex contrast, and choosing the midpoint to be the center location of the complex contrast.

In another embodiment, the step of determining a midpoint comprises the steps of determining the complex contrast of the object, determining the magnitude of the complex contrast, and choosing the midpoint to be the mid-depth of the complex contrast.

In a further embodiment, the midpoint is a spatial component and the step of determining a midpoint comprises choosing the midpoint to be the depth achieved at the maximum measured travel time.

In another embodiment, the midpoint is a temporal component and the step of determining a midpoint comprises choosing the midpoint to be the maximum measured travel time.

BRIEF DESCRIPTION OF FIGURES

FIG. 27 shows a reconstructed image $O_R$ (left) and $O_I$ (right) obtained without analytic continuation for the three-layered structure shown in FIG. 25a.

FIG. 28 shows a reconstructed image $O_R$ (left) and $O_I$ (right) obtained with analytic continuation for the three-layered structure shown in FIG. 25a.

FIG. 29 shows the real (speed) and imaginary (attenuation) parts of the analytically continued trace for the layered structure shown in FIG. 25a.

DETAILED DESCRIPTION

Figure 1:
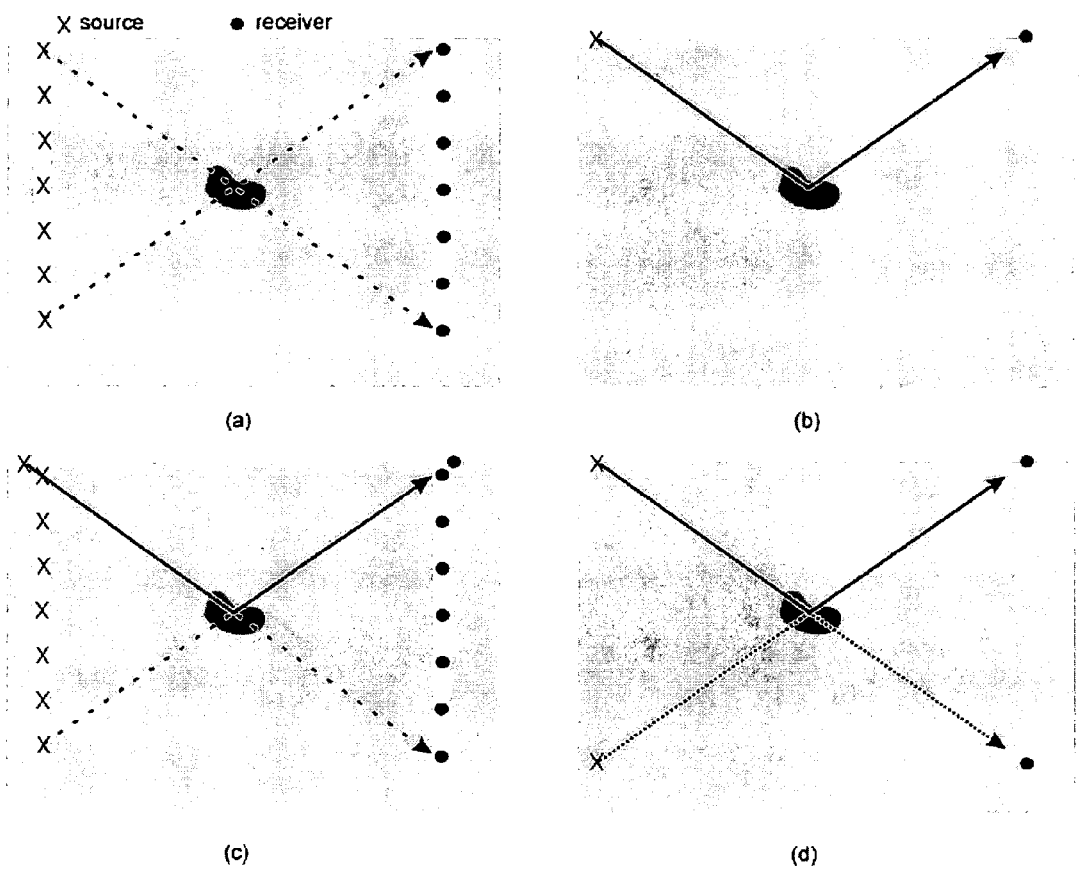
FIG. 1 is a comparison of ray paths for (a) a transmission measurement, (b) a reflection measurement, (c) and overlay of transmission and reflection ray paths, and (d) the supplemental reflection measurement required to produce the same ray path coverage as transmission.

Reconstructing Wave Speed and Attenuation from Limited View Measurements

An incident wave and the recorded scattered wave can be decomposed into superpositions of incident and scattered plane waves. The K-space coverage is defined as the space spanned by the vectors $K = k(s - s_0)$, where k is the wavenumber associated with each temporal frequency component and s and $s_0$ are unit vectors defining directions of propagation of the incident and scattered plane waves, respectively. The characteristics of a scattering object that can be extracted from wave-based measurements will depend on the K-space coverage.

The K-space coverage is some portion of a sphere (the Ewald Sphere) with a radius and voids associated with missing information that depends on both the temporal bandwidth and the particular measurement geometry. For example, transmission measurements yield a K-space coverage that extends out to some distance from the origin and includes the origin. Because the origin is included in the K-space coverage, the spatial DC component of the scattering object can be recovered. In general, reflection measurements are characterized by a K-coverage that extends further from the origin than a transmission K-space coverage and, for this reason, reflection measurements provide better spatial resolution. However, reflection measurements provide no information at the origin of the K-space coverage and, consequently, the spatial DC component of scatterers cannot be determined.

One limiting aspect of reflection measurements is that incident plane waves, $s_0$, have a negative vertical component and the captured scattered plane waves, s, have only positive vertical components, which, if z denotes the vertical direction, produces a K-space coverage over only some portion of an upper hemisphere. The absence of coverage in the lower hemisphere produces a corruption of the information that can be derived for a scattering object's wave speed and attenuation.

This difference in K-space coverage between transmission and reflection measurements can be illustrated by considering ray paths in both measurement configurations. One type of transmission measurement employs parallel linear arrays of sources and receivers. FIG. 1(a) displays such a geometry and two ray paths. While there are many possible ray paths, for illustration purposes only two rays are shown as dashed lines and, for simplicity, these rays are assumed to be straight. This type of measurement geometry, although view limited, provides symmetric K-space coverage and none of the above-mentioned blending of wave speed and attenuation. For comparison, FIG. 1(b) presents a ray path for a reflection measurement where the source and receiver are positioned on the upper surface of the imaged volume. An overlay of the illustrated ray paths is given in FIG. 1(c), and here it is apparent that the reflection ray path partially overlays the transmission ray paths. The transmission measurement geometry yields a symmetric K-space coverage while the reflection geometry does not. For there to be comparable coverage in both configurations, reflection measurements must be made on both the upper and lower surfaces, as in FIG. 1(d).

The previous description has focused on a particular transmission and reflection measurement configuration that, as illustrated in FIG. 1, is two-dimensional. However, the blending of wave speed and attenuation can occur in one-, two-, and three-dimensional measurements where limited views yield asymmetric K-space coverage. The present invention described herein for overcoming this limitation may be used with any dimensionality and measurement geometry.

The Blending of Wave Speed and Attenuation

To demonstrate the effects of blending of a scattering object's wave speed and attenuation, it is sufficient to consider a simple one-dimensional (vertical) problem. Let a scattering object be defined by the complex delta function $f(z)=(A_R+iA_I)\delta(z)$, where $A_R+iA_I$ is the complex contrast having real and imaginary parts that represent the object's wave speed and attenuation, respectively. The Fourier transform of f with respect to z is simply $\tilde{F}(\kappa)=A_R+iA_I$. If this Fourier transform is inverted over $|\kappa|\leq k$ to include the band limited nature of most wave-based information, then we obtain $$\tilde{f}(z) = (A_R + iA_I)\int_{-k}^{k} e^{i\kappa z} dz = (A_R + iA_I)\frac{2}{z}\sin(kz), \quad (1)$$

which is an exact reconstruction of the delta function within the bandwidth limitations. It should be noted that, for reflection measurements, there is no information at $\kappa=0$. However, excluding such information is peripheral to the present analysis.

If knowledge of $\tilde{F}$ is restricted to $\kappa \geq 0$, then the inverse Fourier transform becomes $$\tilde{f}^+(z) = (A_R + iA_I)\int_0^k e^{i\kappa z} dz \quad (2)$$
$$= (A_R + iA_I)\left\{\frac{\sin(kz)}{z} + \frac{1}{z}[1-\cos(kz)]\right\},$$

where the superscripted plus sign is intended to explicitly indicate that information for $\kappa \geq 0$ is included. The reconstructed function $\tilde{f}^+$ can be decomposed into real and imaginary parts as follows:

$$\tilde{f}_R^+(z) = A_R\frac{\sin(kz)}{z} - A_I\frac{1}{z}[1-\cos(kz)], \text{ and,} \quad (3)$$
$$\tilde{f}_I^+(z) = A_I\frac{\sin(kz)}{z} + A_R\frac{1}{z}[1-\cos(kz)].$$

Taking f to be real, it follows that $A_I=0$, so that $$\tilde{f}_R^+(z) = A_R\frac{\sin(kz)}{z},$$

which has half the correct amplitude given in Eq. (1). If it known that f is real, then coverage can be analytically continued into $\kappa<0$ giving the correct reconstruction $\tilde{f}=2*\Re[\tilde{f}^+]$. If there is no a priori knowledge about the contrast of f but if there is no attenuation ($A_I$), then the reconstructed $\tilde{f}^+$ is given by:

$$\tilde{f}_R^+(z) = A_R\frac{\sin(kz)}{z}, \text{ and,} \quad (4)$$
$$\tilde{f}_I^+(z) = A_R\frac{1}{z}[1-\cos(kz)],$$

and it is clear that the shape of $\tilde{f}_R^+$ is correct but its amplitude is one-half the correct value. Further, it is clear that there is spurious attenuation, $\tilde{f}_I^+$, that is of the same order as the reconstructed wave speed variations. It should be reiterated that the shape of $\tilde{f}^+$ is still correct—unlike the situation in which the scatterer is complex and the reconstruction is given by Eq. (3). In that case, both $\tilde{f}_R^+$ and $\tilde{f}_I^+$ are in influenced by the complex contrast $A_R+iA_I$. Further, since $\sin(\kappa z)/z$ is an even function of z and $(1/z)[1-\cos(kz)]$ is an odd function of z, the shape of $\tilde{f}^+$ will be corrupted.

Figure 2:
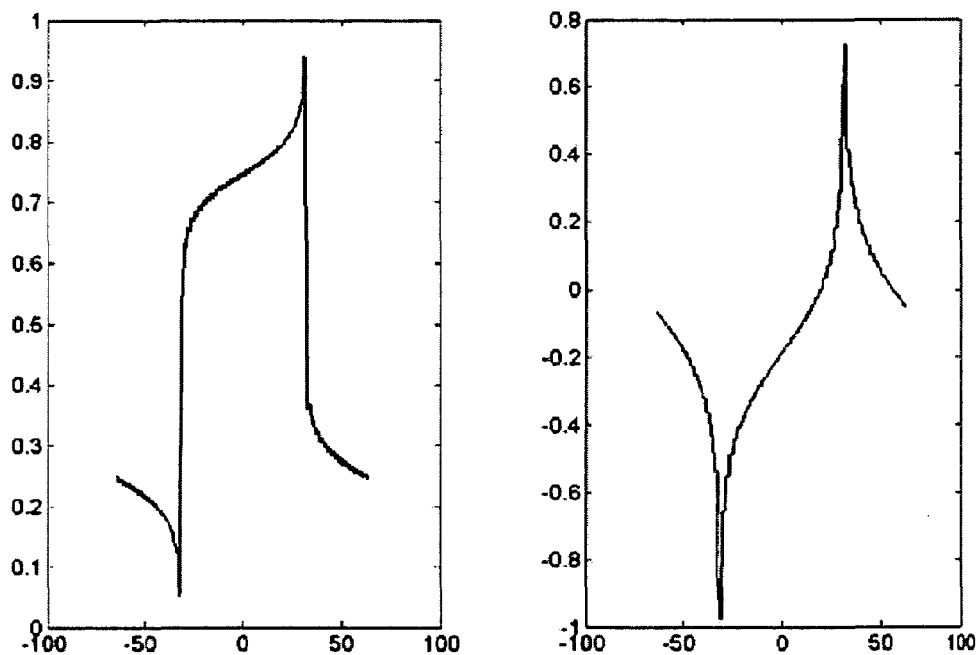
FIG. 2 is a reconstructed image of the real part (left) and imaginary part (right) of a complex top-hat where information has been limited to $\kappa \geq 0$.

To illustrate the shape corruption that will result from the inseparable blending of speed and attenuation, consider the complex top-hat function $f(z)=A_R+iA_I$ for $|z|\leq b$ and zero otherwise. FIG. 2 shows the reconstructions of $\tilde{f}_R^+$ and $\tilde{f}_I^+$ for $A_R=1$ and $A_I=-0.25$. The shape corruption caused by the blending of wave speed and attenuation is clearly evident in the reconstructions of both $\tilde{f}_R^+$ and $\tilde{f}_I^+$.

Reconstructing Wave Speed and Attenuation

Figure 3:
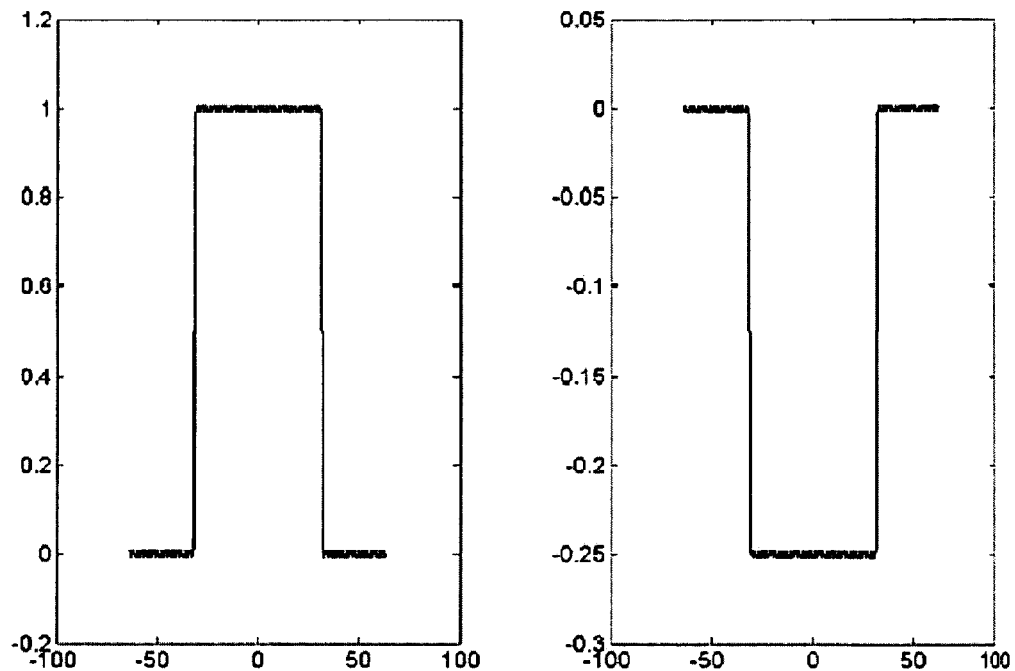
FIG. 3 is a reconstructed image of the real part (left) and imaginary part (right) of a complex top-hat where information has been extended to $|\kappa| \geq 0$ by requiring the shape to be an even function.

In order to properly recover a scattering object's shape and its complex contrast, it is necessary to somehow introduce information over $\kappa<0$ in one dimension where, for two- or three-dimensional measurements, K must be extended beyond $K=k(s-s_0)$ so as to yield symmetric K-space coverage. This result can be accomplished by recognizing that, for objects of interest, the properties of the object are constant. In this case, the object is described by a constant complex contrast $A_R+iA_I$ and a shape function S that is a real constant within its support volume. This requires that S be an even function so that its spatial Fourier transform, $\tilde{S}$, can be analytically extended by specifying that $$\tilde{S}(\kappa)=\tilde{S}(-\kappa), \tag{5}$$

in one-dimension and $\tilde{S}(K)=\tilde{S}(-K)$ in two and three dimensions, where K is a wavevector and $\kappa$ is a scalar wavenumber (a one-dimensional wavevector). Applying this procedure to the complex top hat function previously introduced yields the reconstruction shown in FIG. 3. Both the contrast and the shape are properly reconstructed, and the result is far superior to that offered by $\tilde{f}^+$ (FIG. 2).

Figure 4:
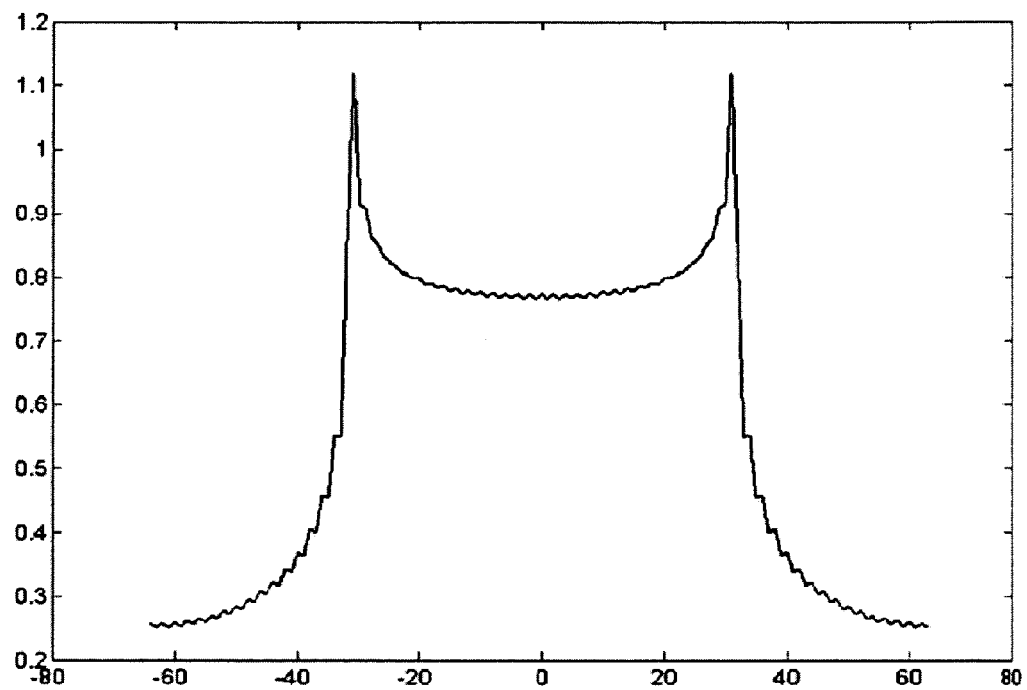
FIG. 4 is a plot of $|\tilde{T}^+|$ where $\tilde{T}^+$ is shown in FIG. 2.

The analytic continuation given by Eq. (5) will fail when the object is vertically offset. This failure occurs because, for an object centered at $z=z_0$, a phase shift of $-\kappa z_0$ will be introduced into $\tilde{F}$, and the imposition of Eq. (5) will alter this phase shift. In the more general case of objects having an arbitrary location, it is necessary to apply Eq. (5) on an object-by-object basis where the location of each object is first determined. A phase shift of $\kappa z_0$ is applied to $\tilde{F}$ to move it to the origin, Eq. (5) is then applied, and finally the object is phase shifted back to the proper location. There are many ways to quantify the location of an object even when its shape has been corrupted as shown in FIG. 2. For example, inspection of $|\tilde{f}^+|$ (FIG. 4) rather than $\tilde{f}^+$ will yield a rectified image of f that has well defined boundaries from which the object's location can be determined, but not necessarily the correct shape and contrast.

The analytic continuation given by Eq. (5) can be extended to measurement configurations where there is an absence of K-space coverage in directions other than or in addition to the vertical direction. In these situations, the more general form, $$\tilde{S}(K)=\tilde{S}(-K), \tag{6}$$

can be used.

Reconstructing Images of Wave Speed and Attenuation

For purposes of illustration, image reconstruction will be demonstrated below for a two-dimensional vertical cross-section. Again, those of skill in the art will recognize that the application of this concept to three-dimensional imaging is a straightforward extension. It is assumed here that an array of receivers is positioned on the ground surface ($z=0$) and that the position of a particular receiver is denoted by l. For simplicity, the illumination of the subsurface is assumed to be by a plane wave propagating straight down so that the incident field in the frequency domain is given by $u_0(r)=e^{-ikz}$. Other forms of illumination may be used with equal validity provided that data is available for an array of source location. Furthermore, this approach to image reconstruction of wave speed and attenuation is valid for multi-monostatic measurements such as those typically found in ground penetrating radar where source and receiver are moved in unison at a fixed separation along the ground surface.

The formulation presented here is the linearized theory based on the Born approximation and is implemented in the temporal- and spatial-frequency domain. Let u(l,t) denote the acquired real data as a function of time t at every receiver location l. The processed data $\tilde{u}(\kappa,\omega)$ is the double Fourier transformed u, $$\tilde{u}(\kappa,\omega)=\int_{-\infty}^{\infty}dl e^{i\omega t}\int_{-\infty}^{\infty}dt e^{-i\kappa l}u(l,t). \tag{7}$$

The desired image quantity is the "object function" that describes the spatial variations in complex wave speed c(r) relative to a background wave speed $c_0$. Specifically, the object function is defined as $$O(r)=1-\frac{c_0^2}{c^2(r)} \tag{8}$$

and, for simplicity and without loss of generality, it is assumed here that $c_0$ is real so that the real and imaginary parts of O directly indicate the real (wave speed) and imaginary (attenuation) parts of c(r). An analytic relationship exists, known as the generalized projection slice theorem, that relates the two-dimensional spatial Fourier transform of the object function to the temporal-spatial Fourier transform of u ($\tilde{u}$ given by Eq. (7)). (See Devaney, A. J., 1982, "A filtered back propagation algorithm for diffraction tomography," ULTRASONIC IMAGING, 4, 336–350.) For the specific geometry considered here, this relationship is given by $$\tilde{O}(K)=2i\frac{\sqrt{k^2-\kappa^2}}{k^2}\tilde{u}(\kappa,\omega), \tag{9}$$

where $k=\omega/c_0$ is the background wavenumber at frequency co and the wavevector K is given by $$K=(K_x,K_z)=(\kappa,\sqrt{k^2-\kappa^2}+k). \tag{10}$$

Equation (9) can be used to determine $\tilde{O}$ from the acquired data $\tilde{u}$, and the complex object function can be computed by numerically inverting the two-dimensional Fourier transform using the relationship $$dK_x dK_z=\frac{\sqrt{k^2-\kappa^2}+k}{\sqrt{k^2-\kappa^2}}d\kappa d\omega.$$

Figure 5:
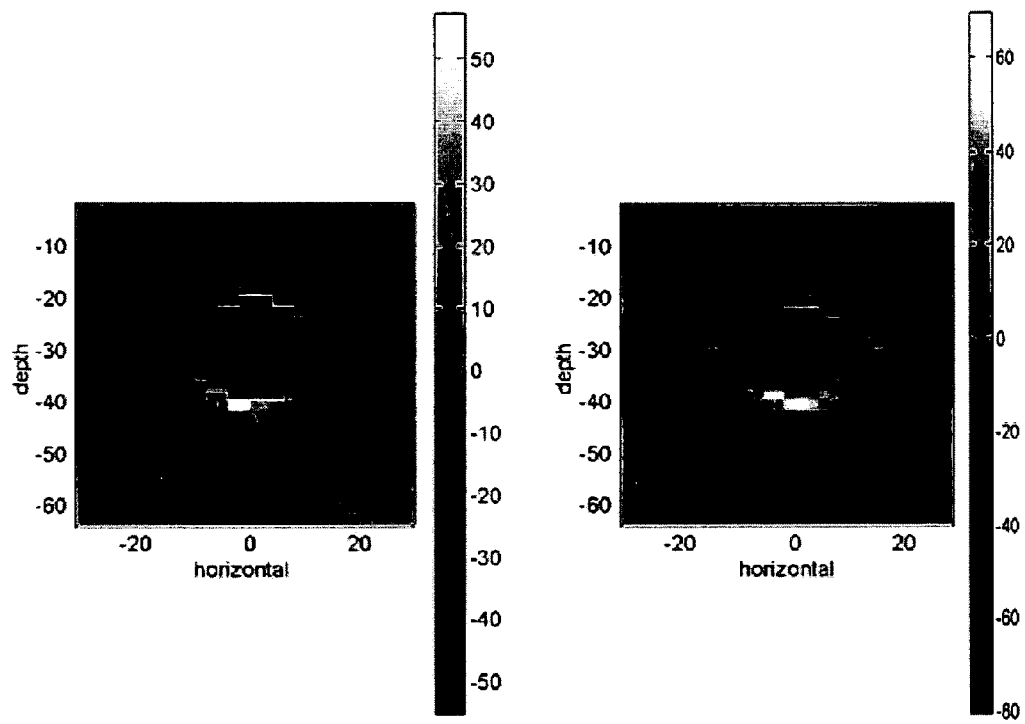
FIG. 5 is a reconstructed image over a vertical cross-section of wave speed (left) and attenuation (right) for a circle with complex contrast $A_R = A_I = 1$.

This reconstruction will yield corrupted images of the wave speed (the real part of O) and the attenuation (the imaginary part of O) in the same manner as that discussed in the one-dimensional formulation (FIG. 2). Once again, this is an issue associated with the blending of real and imaginary parts that cannot properly be separated in this measurement geometry and is directly linked to the so-called K-space coverage. In the one-dimensional problem, it was assumed that the Fourier transform of some function f was known only on a line segment where $\kappa\geq 0$. This same limitation exists in the two-dimensional problem considered here, where knowledge of $\tilde{O}$ is limited to some portion of the half-space $K_z\geq 0$. Taking the support of O to be a circle of specified radius and, within this support, O to be a complex constant $O=A_R+iA_I$, then the data $\tilde{u}$ can be synthesized and an image reconstructed based on Eq. (9). If the resulting image is perfect, it should be a reconstruction of circles having contrasts $A_R$ and $A_I$ for the real and imaginary parts of O, respectively. For a circle of radius 10 at a depth of 15, data (ũ) has been synthesized for an array of 32 receivers spaced at intervals of 2 units located symmetrically above the center of the circle. At each receiver, 128 time samples are synthesized at a temporal sampling interval of $0.5 \times 10^{-3}$. FIG. 5 displays the reconstructed image of both speed (left) and attenuation (right) for a complex contrast $A_R=A_I=1$. If these images had no corruption from blending, they would, for the specified contrast, be identical. This is clearly not the case, and thus the imaging procedure, as implemented, has not successfully individually reconstructed speed and attenuation.

Figure 6:
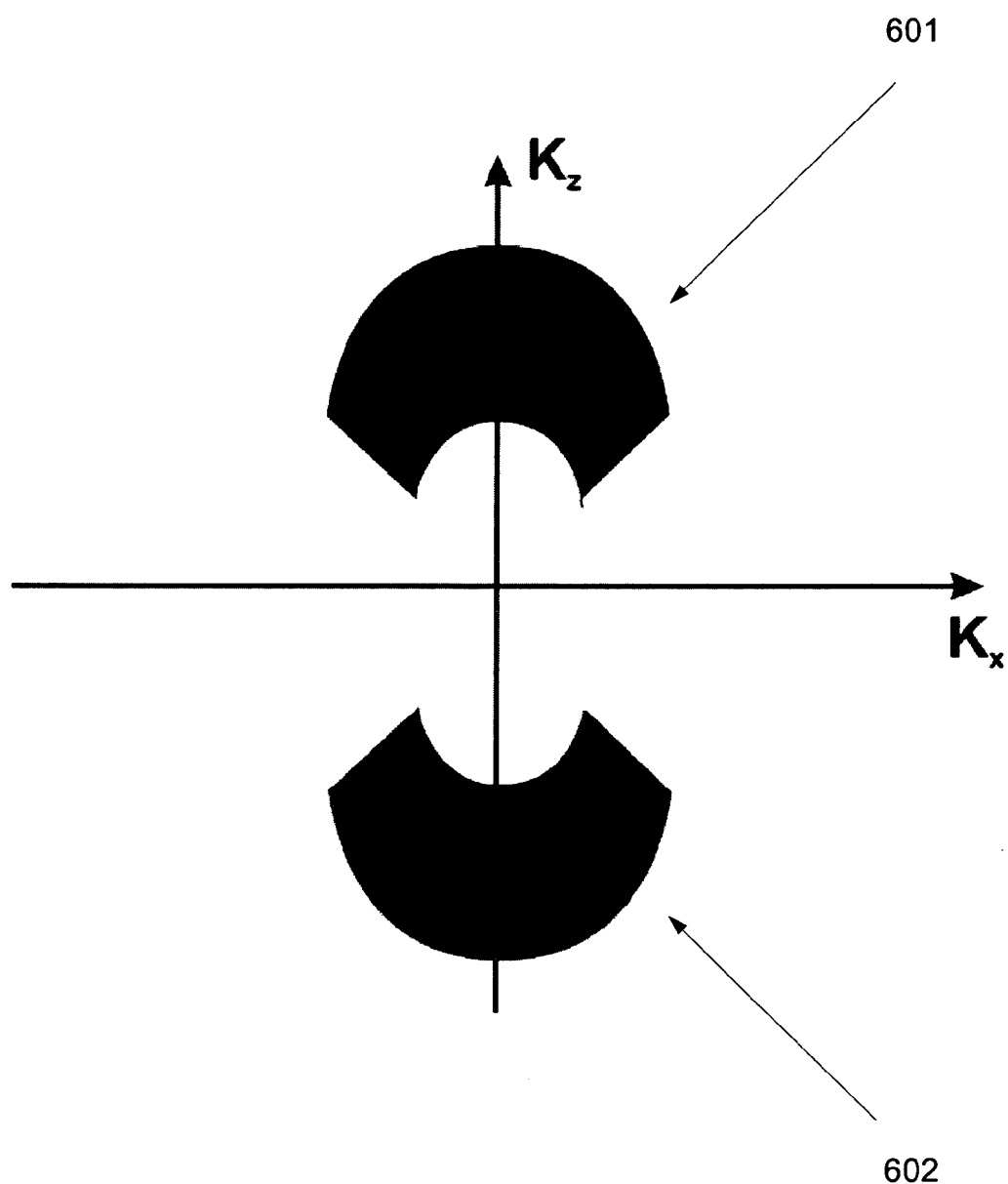
FIG. 6 illustrates the actual K-space coverage (black) for measurement geometry considered in the present application and that added by analytic continuation (gray).
Figure 7:
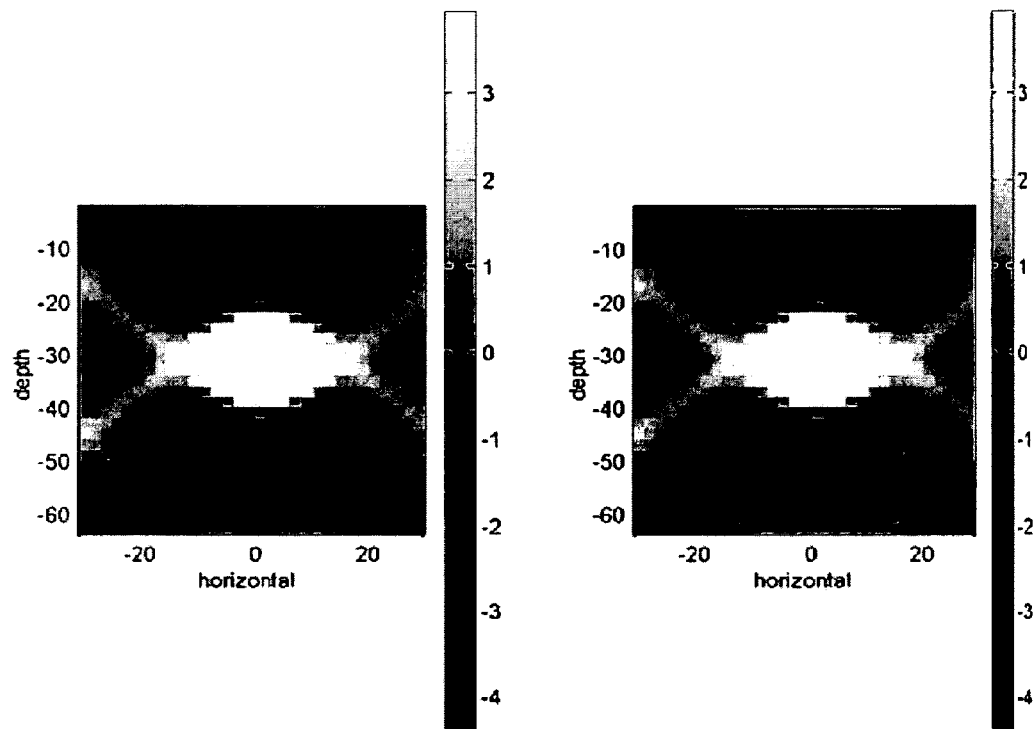
FIG. 7 is a reconstructed image over a vertical cross-section of wave speed (left) and attenuation (right) for a circle with complex contrast $A_R = A_I = 1$ after the application of analytic continuation.

However, the corruption of real and imaginary parts of O from blending can be removed by analytic continuation as previously discussed. The requirement that O be an even function is imposed on Õ as $Õ(-K)=Õ(K)$. The K-space coverage for measurement geometry considered here is shown as area 601 in FIG. 6. It is clear that this coverage is symmetric in $K_x$ so that it is necessary only to impose $Õ(-K_z)=Õ(K_z)$ to provide the analytically continued coverage depicted by area 602 on FIG. 6. If all parameters are identical to those used for FIG. 5, then FIG. 7 displays the reconstructed image after analytic continuation. Here, the real and imaginary parts of the image are nearly identical, differing only in the magnitude of the contrast. This contrast difference is not a result of the analytical continuation but does depend on K-space coverage. As evident in FIG. 6, there is no K-space coverage at the origin, which means that the spatial DC component of the image is lost. This is a manifestation of the reflection geometry and is independent of the analytic continuation.

Reconstituting the Data by Analytic Continuation

Figure 8:
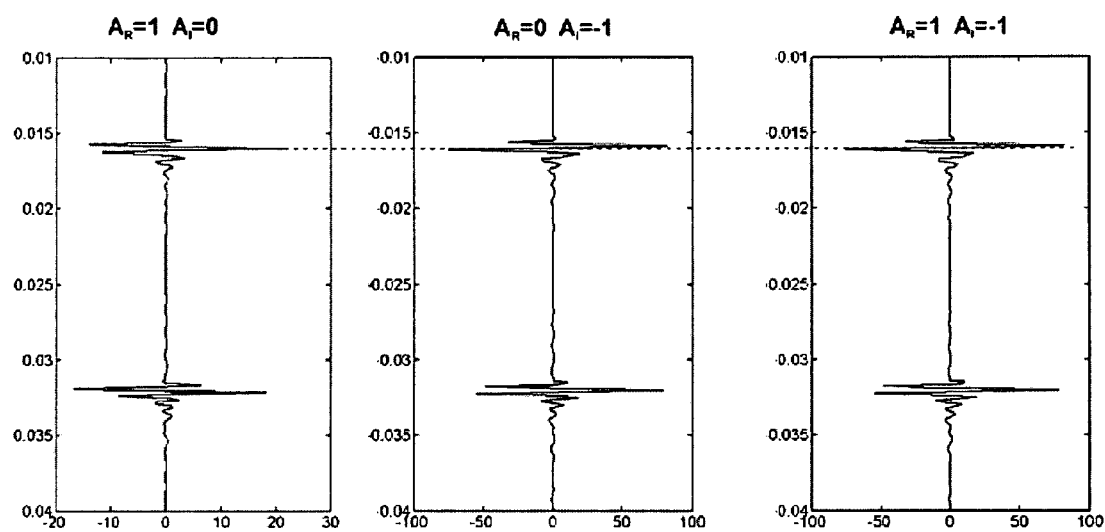
FIG. 8 shows synthetic traces acquired directly above a buried circular feature for a real contrast $A_R = 1$ and $A_I = 0$ (left), and imaginary contrast $A_R = 0$ and $A_I = -1$ (center), and a complex contrast $A_R = 1$ and $A_I = -1$ (right).

In time-domain reflection measurements, a record of the received signal amplitude is recorded as a function of time at every receiver location. Each of these series is referred to here as a trace, and each trace is real. Reflections from spatial variations in both wave speed and attenuation are blended into each trace and, in this form of the data, the individual effects of wave speed and attenuation are inseparable. To demonstrate this fact, simulated traces are presented for a buried circular inclusion having a radius of 10 units buried at a depth of 30 units embedded in a material having a wave speed of 2500 units/sec. An array of 32 receivers spaced at intervals of 2 units is used, and 512 time samples are synthesized at uniform time intervals of $0.125 \times 10^{-3}$ sec. The only change among simulations is the complex contrast of the circle, which again is defined as $A_R$ and $A_I$ for the relative speed and attenuation contrast, respectively. FIG. 8 shows time-windowed portions of traces from a receiver located directly over the top of the circle for three different contrasts. All three traces show reflections from both the top and bottom of the circle, and these traces are quite similar with contrast differences manifested only in the amplitude of the reflections and a slight phase shift that becomes apparent when individual peaks are compared to the dashed line.

Figure 9:
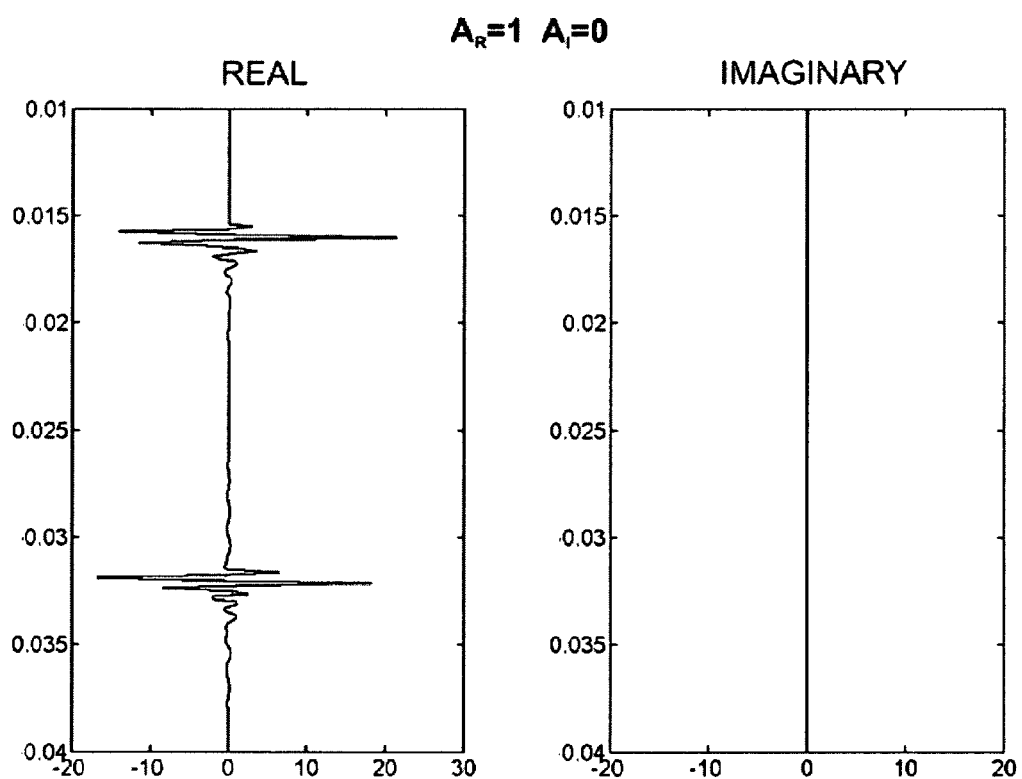
FIG. 9 shows the real and imaginary parts of the analytically continued trace for an object with a real contrast (FIG. 8, left).
Figure 10:
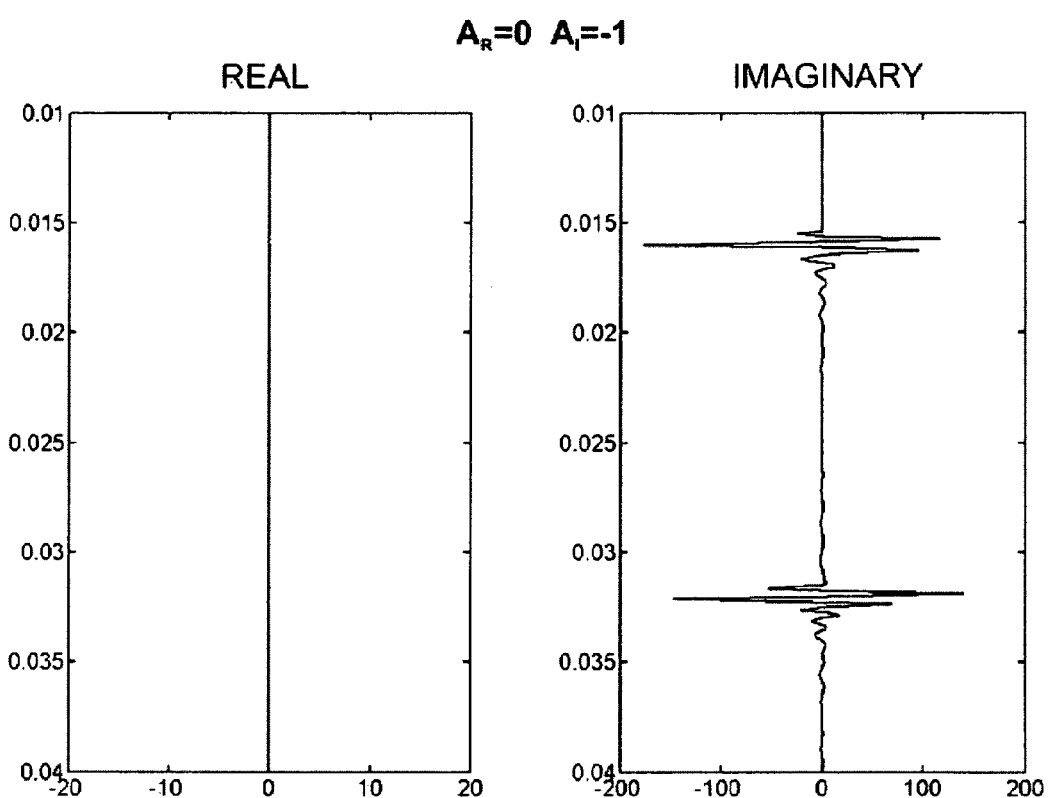
FIG. 10 shows the real and imaginary parts of the analytically continued trace for an object with an imaginary contrast (FIG. 8, center).
Figure 11:
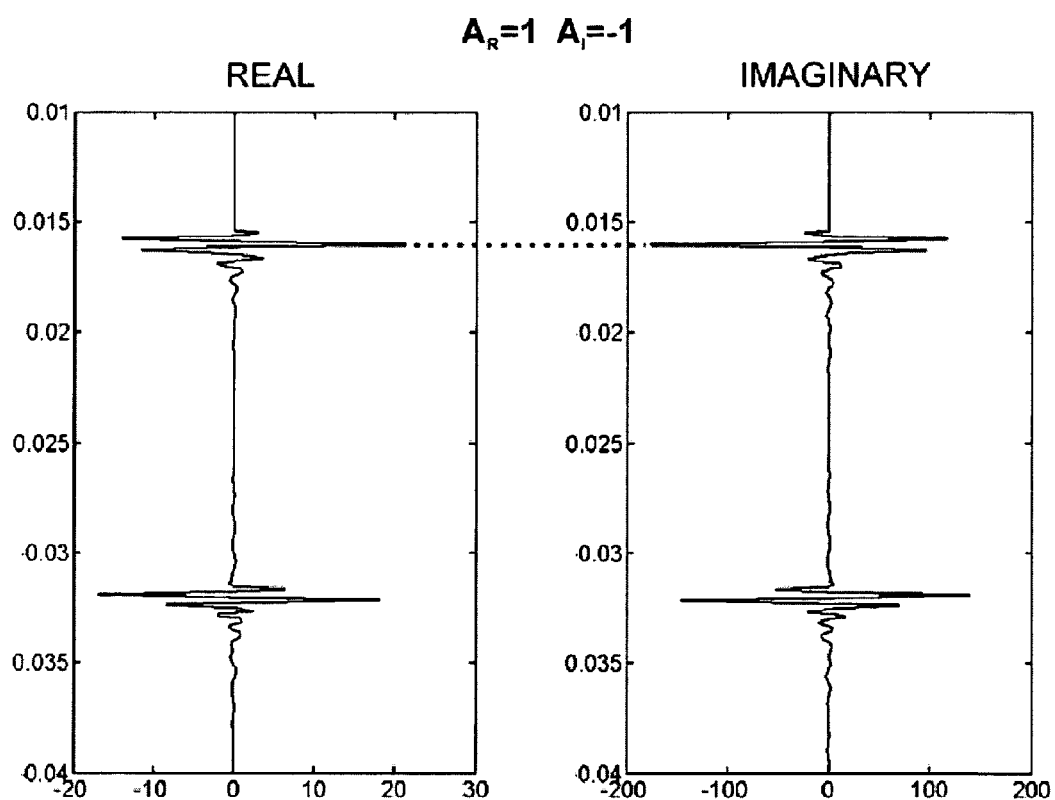
FIG. 11 shows the real and imaginary parts of the analytically continued trace for an object with a complex contrast (FIG. 8, right).

The spatial and temporally Fourier transformed data ũ may be analytically continued by the analytic continuation of $Õ(Õ(-K_z)=Õ(K_z))$ and by applying Eq. (9). The original data u(l,t) is real so that the Fourier transformed data ũ is Hermetian symmetric. The analytic continuation of ũ destroys this symmetry and, as a result, the reconstituted data recovered by inverting the spatial and temporal Fourier transforms is complex. Thus, this form of analytic continuation produces a single complex trace from every real trace. FIG. 9 presents the real and imaginary traces derived from the analytic continuation of the real trace shown on the left of FIG. 8. This result is for a real contrast, i.e., one that has only a contrast in wave speed. These two traces can be thought of as a wave speed response trace and an attenuation response trace. For this particular trace, the reflection is a result of only a contrast in wave speed, and the analytically continued data properly represents this fact by producing a reflection in the real part (speed) and none in the imaginary part (attenuation). The converse is true for an attenuation-only contrast (FIG. 10). Here, a reflection appears only in the imaginary trace. When the contrast is complex, i.e., a contrast in both wave speed and attenuation, reflections appear in both the real and imaginary traces (FIG. 11). The dashed line is included in FIG. 11 to confirm that there is no phase shift between real and imaginary peaks.

Figure 12:
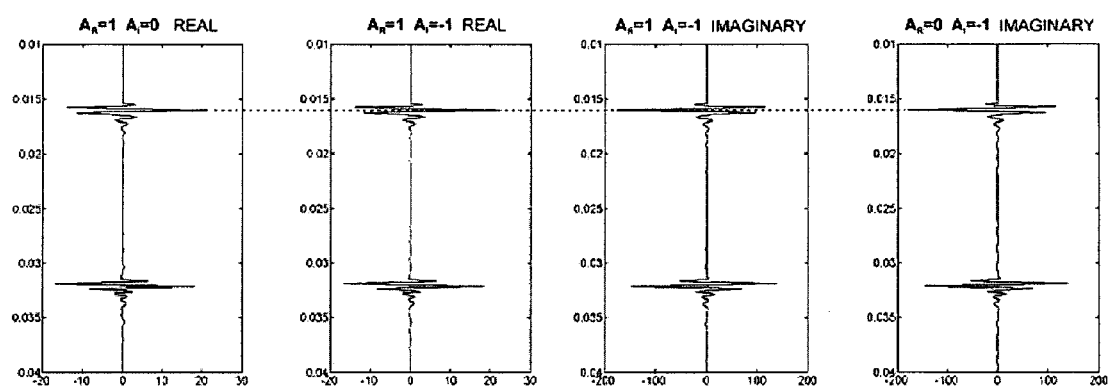
FIG. 12 is a comparison of results of reconstituting data for three different contrasts.

The results of the analytic continuations for the three contrasts are compared in FIG. 12. The real and imaginary traces for the complex contrast object (FIG. 11) appear in the center of FIG. 12. The real trace for the real contrast object (FIG. 9) is on the left. The real contrast component for both of these objects is the same, $A_R=1$, and, as such, the real trace for both should also be the same. It is clear from FIG. 12 that this is in fact the case. Similarly, the complex contrast object and the imaginary contrast object have the same imaginary contrast, $A_I=-1$ and should also be identical. The imaginary trace from the imaginary object is shown on the extreme right of FIG. 12 and it is again apparent that these two traces are identical. The dashed line on FIG. 12 is used for phase reference, and it clear that, after reconstituting the data, there is no relative complex contrast induced phase shift. This result is of particular importance since a phase shift induced by a complex contrast will introduce errors in depth estimation.

Processing Real Ground Penetrating Radar Data

Ground penetrating radar (GPR) employs electromagnetic waves and, for these types of waves, wave speed and attenuation will depend on dielectric and electrical conductivity. For these reason, separated images of wave speed and attenuation can provide insight into the material properties of scattering objects. The most common type of GPR data acquisition uses a reflection measurement geometry where a single transmitting and receiving antenna are moved in unison along the ground surface maintaining a fixed separation. Because this geometry is a limited view reflection geometry, it implicitly possesses the same problems in the blending of real and imaginary parts of O(r) as previously considered. For purposes of illustration, the analytic continuation procedure is applied to an actual GPR data set where the K-space coverage, actual and continued, is similar to the one shown in FIG. 6, and the wave vector over which Õ(K) is known is slightly different from that given in Eq. (10). Specifically, K is given by $$K=(K_x,K_z)=(\kappa, \sqrt{4k^2-\kappa^2}). \quad (11)$$

Figure 13:
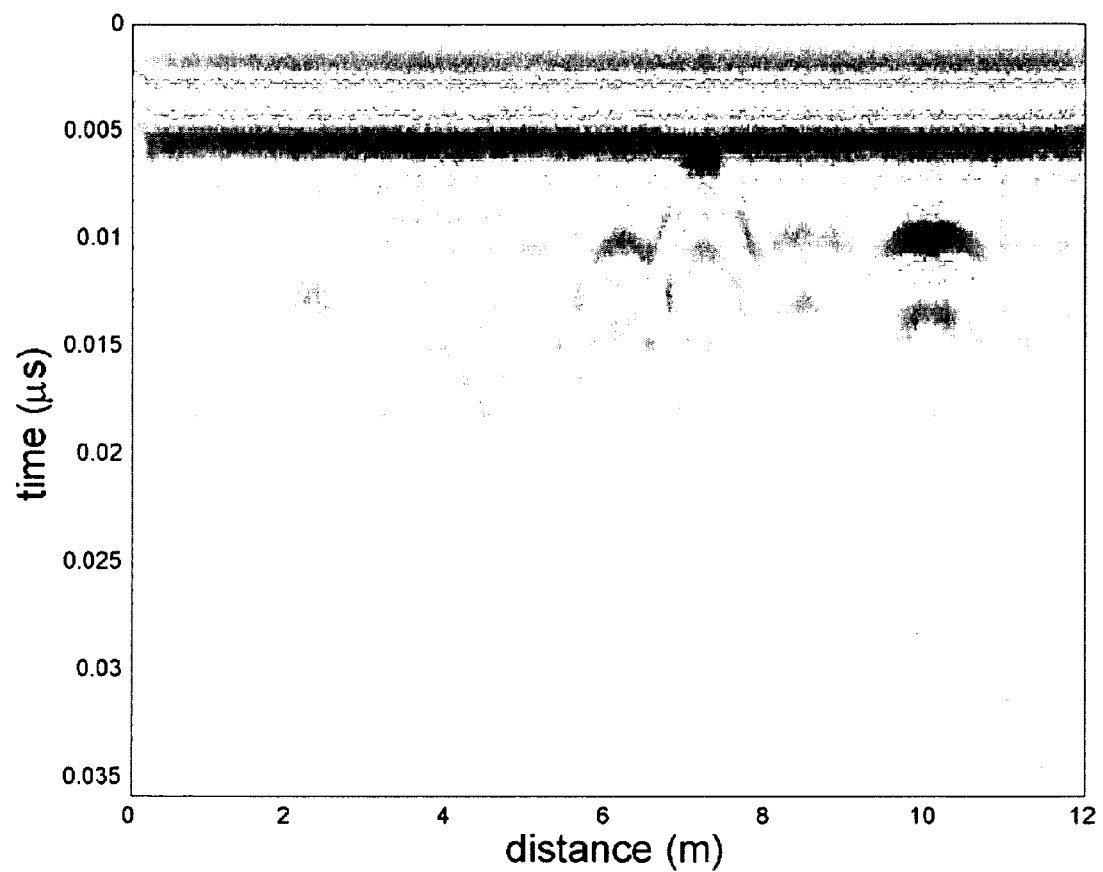
FIG. 13 illustrates ground penetrating radar data acquired over eight buried objects.

The acquired GPR data is shown in FIG. 13, and the eight known buried objectives are manifested in this data as hyperbolas. From left to right, these eight objects are:

(1) a 60 cm by 30 cm polystyrene tube,
(2) a 60 cm by 15 cm polystyrene tube,
(3) a 60 cm diameter concrete tube,
(4) a 20 cm diameter PVC tube,
(5) a 6.35 cm diameter iron tube,
(6) a 6.35 cm diameter iron tube,
(7) a 60 cm by 4 cm wood disk, and,
(8) a 60 cm by 4 cm iron disk.

This data is appropriate for rigorously testing the analytic continuation procedure because these objects are known and offer a variety of materials that produce reasonably well known changes in wave speed and attenuation. For this data, spatial and temporal sampling are 3 cm and 0.2 ns, respectively.

Figure 14:
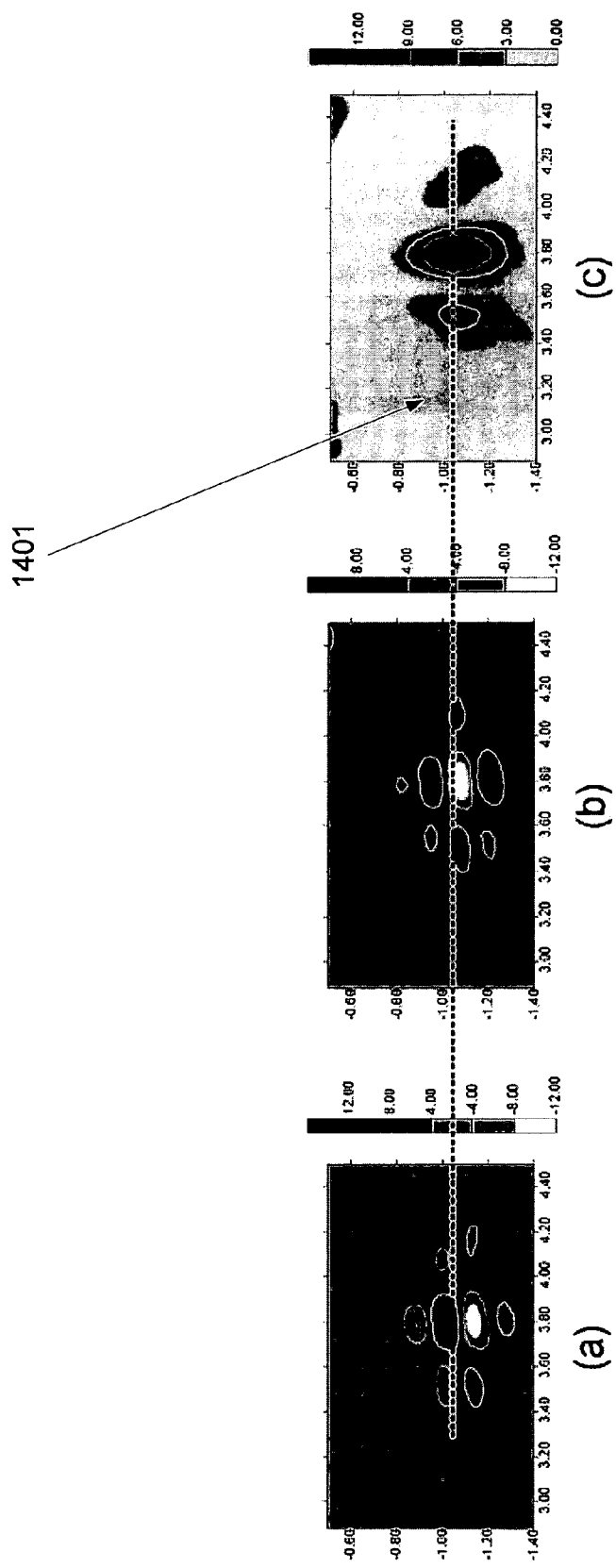
FIG. 14 shows vertical cross-sectional images of (a) $O_R$, (b) $O_I$, and (c) $|O|$ reconstructed for the concrete tube (Target 3) without using analytic continuation.

Vertical cross-sectional images of the concrete tube (Target 3) reconstructed without analytic continuation are shown in FIG. 14, where the magnitude of the object function is defined to be $|O| = \sqrt{O_R^2 + O_I^2}$ and $O_R$ and $O_I$ are the real and imaginary parts of O, respectively. The dashed line 1401 in FIG. 14 indicates what should be the approximate mid-depth of the concrete tube. Comparing the real (FIG. 14a) and imaginary (FIG. 14b) parts of O, it is clear that they do not yield images at a consistent depth, which is an effect of the blending of speed and attenuation. It should further be noted that the image of |O| provides a better shape of the circular tube than either $O_R$ or $O_I$. Reflection geometries provide no K-space coverage at the origin (FIG. 6) and, as such, the images can appear hollow. Experience with reflection-based image reconstruction has shown that the information around the K-space origin is artificially introduced such the contrast of the reconstructed feature has a zero mean. For example, an object that has a positive wave speed contrast with respect to its background will have a negative contrast in the center, and vice versa. This is what has happened in FIG. 14a and FIG. 14b. By virtue of the definition of |O|, the feature of interest has a near-uniform positive contrast throughout (FIG. 14c) making the image solid, but the sign of the contrast is lost.

Figure 15:
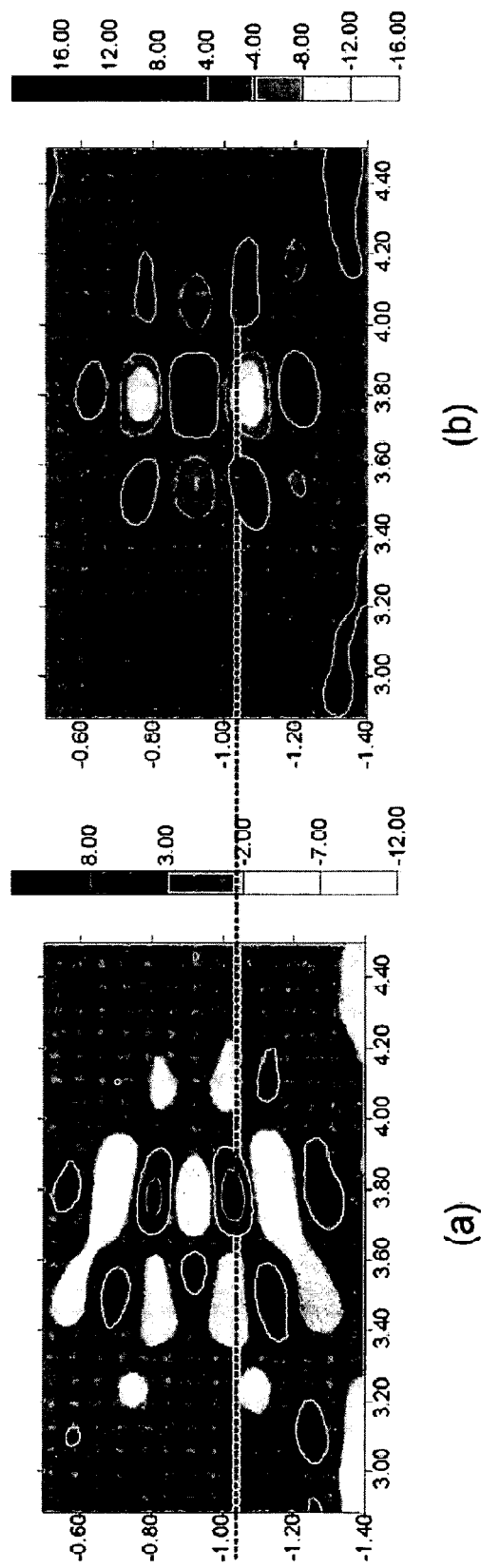
FIG. 15 shows vertical cross-sectional images of (a) $O_R$ and (b) $O_I$ reconstructed for the concrete tube (Target 3) using analytic continuation.

Reconstructed images of $O_R$ and $O_I$ for the concrete tube with the application of analytic continuation are given in FIG. 15. As previously discussed, in applying analytic continuation, it is necessary to spatially phase shift the manifestation of each object to the origin and then reverse this phase shift after the analytic continuation. To accomplish this here, the mid-depth of the object is taken to be the depth of the maximum of |O| (FIG. 14c). The ringing that is apparent in these images is a result of bandwidth limitation (images are reconstructed using 29 frequencies uniformly distributed between 24 and 542 MHz) that limits K-space coverage. This ringing appears more severe in the images reconstructed with analytic continuation than those without. This difference could, in part, be a result of difference plotting contrasts employed in the display or a slight error in locating the mid-depth of the object. It is clear from an inspection of FIG. 15 that images of both $O_R$ and $O_I$ are relatively consistent in depth and that the circular concrete tube has a wave speed ($O_R$) that is less than the background and an attenuation ($O_I$) that is greater than the background.

Figure 16:
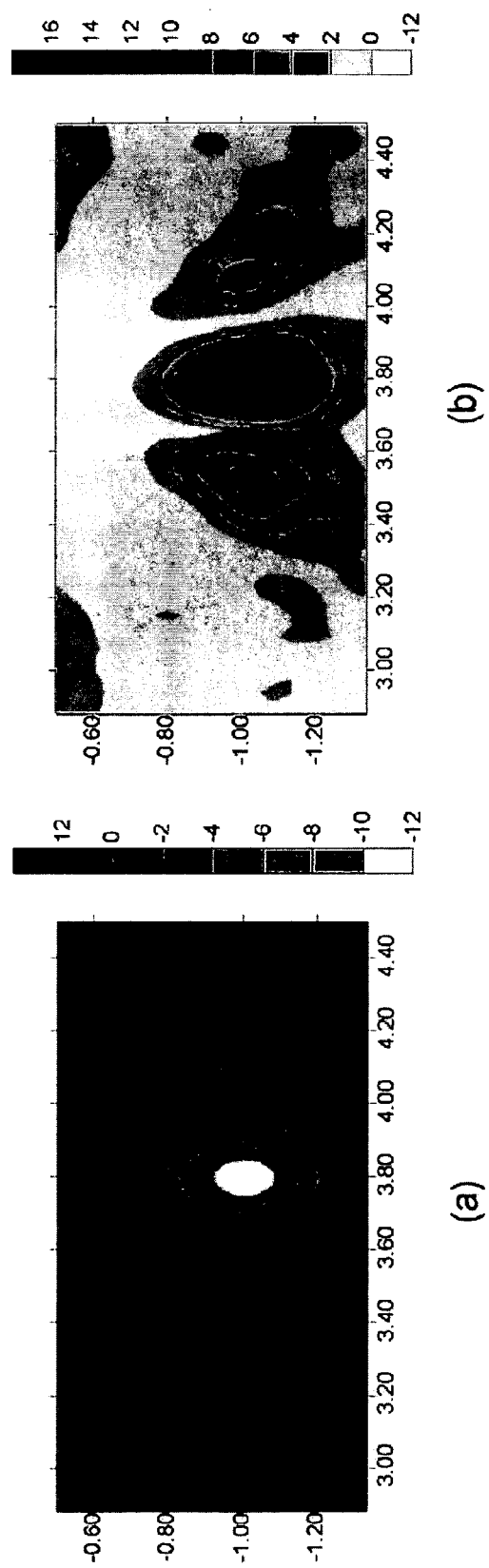
FIG. 16 shows vertical cross-sectional images of (a) $O_R$ and (b) $O_I$ reconstructed for the concrete tube (Target 3) using analytic continuation for the contrast and $|O|$ for the shape.

One way to exploit the fact that the reconstruction of |O| yields a better shape is to retain this shape but to associate with it the contrast provided by the analytically continued images of $O_R$ and $O_I$. This is done in FIG. 16, where the shapes of the two images are identical, but their contrasts differ and represent those determined from FIG. 15.

Figure 17:
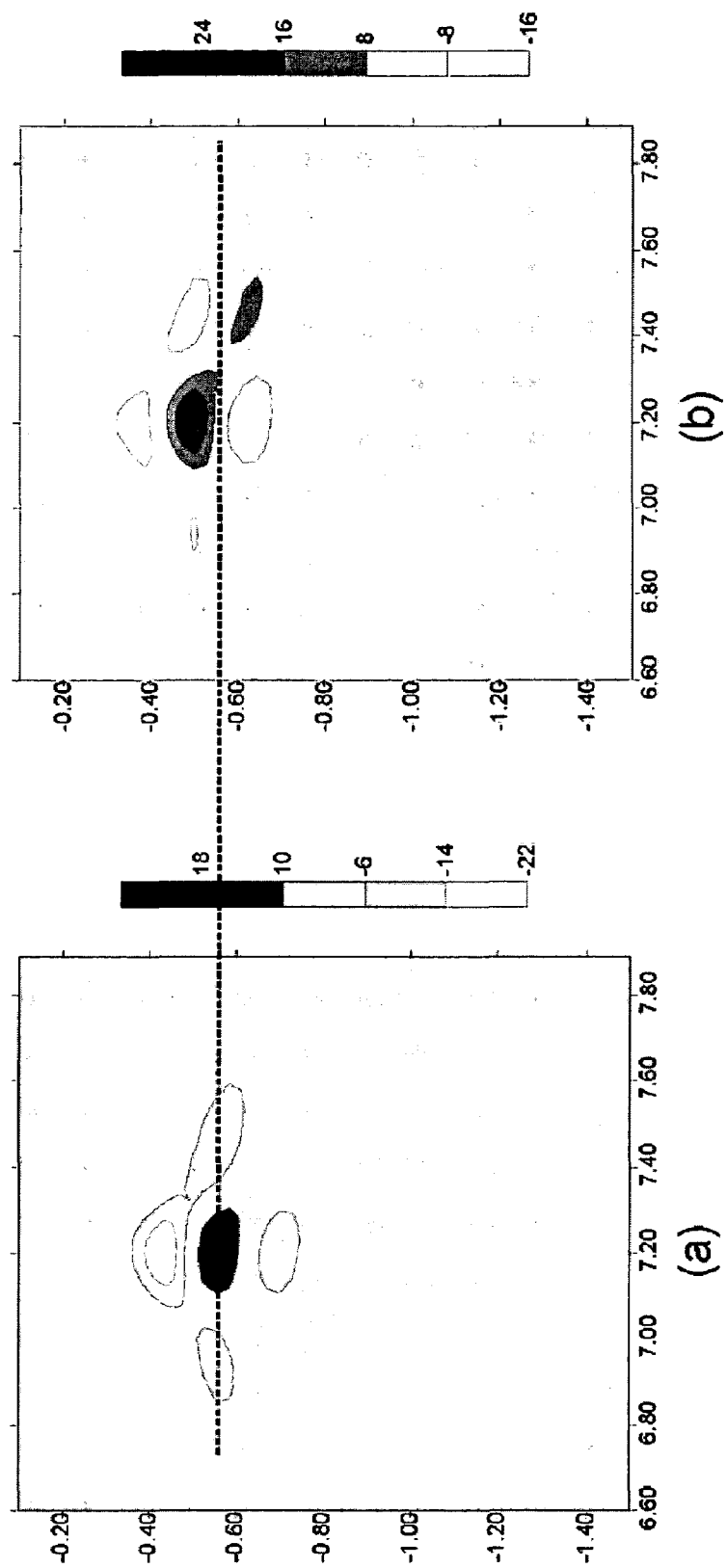
FIG. 17 shows vertical cross-sectional images of (a) $O_R$ and (b) $O_I$ reconstructed for the iron tube (Target 6) without using analytic continuation.
Figure 18:
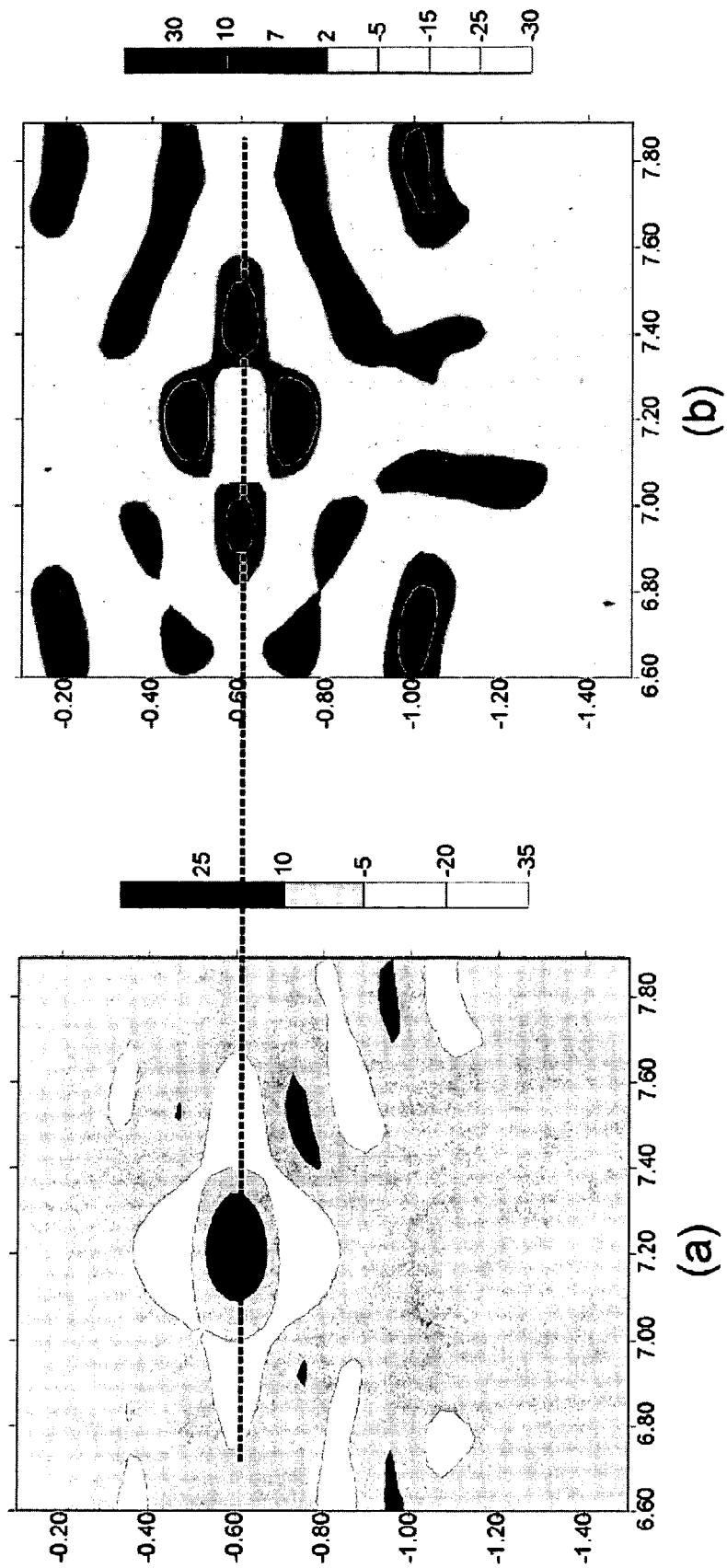
FIG. 18 shows vertical cross-sectional images of (a) $O_R$ and (b) $O_I$ reconstructed for the iron tube (Target 6) using analytic continuation.

The host dry sand has a relatively high electromagnetic wave speed and little or no attenuation. The images reconstructed here use a spatial Fourier transform-based algorithm and, hence, it is assumed that there is no background attenuation. The concrete tube, as imaged in FIGS. 14, 15, and 16, should exhibit a decrease in wave speed and an increase in attenuation relative to the background. This trend is properly represented in the images shown in FIGS. 15 and 16. Target 6 is an iron tube and should also show the same trend as the concrete tube, but with greater contrasts in both wave speed and attenuation. FIG. 17 illustrates the reconstructed images of $O_R$ and $O_I$ for this target without analytic continuation. The dashed line 1701 in FIG. 17 is used as a depth reference, and it is clear that there is a vertical shift between these two images. The reconstructed wave speed is less than the background, which is to be expected. However, the contrast for the attenuation, FIG. 17b, is reversed. It appears to be less attenuating than the background when, in fact, it should be considerably larger. The images of $O_R$ and $O_I$ for Target 6 reconstructed with analytic continuation are given in FIG. 18, and it is clear that the iron tube appears at the same depth and with the proper contrast, i.e., the wave speed contrast is negative and the attenuation contrast is positive. Further, the contrasts of both attributes are, as expected, greater than those for the concrete tube.

Figure 19:
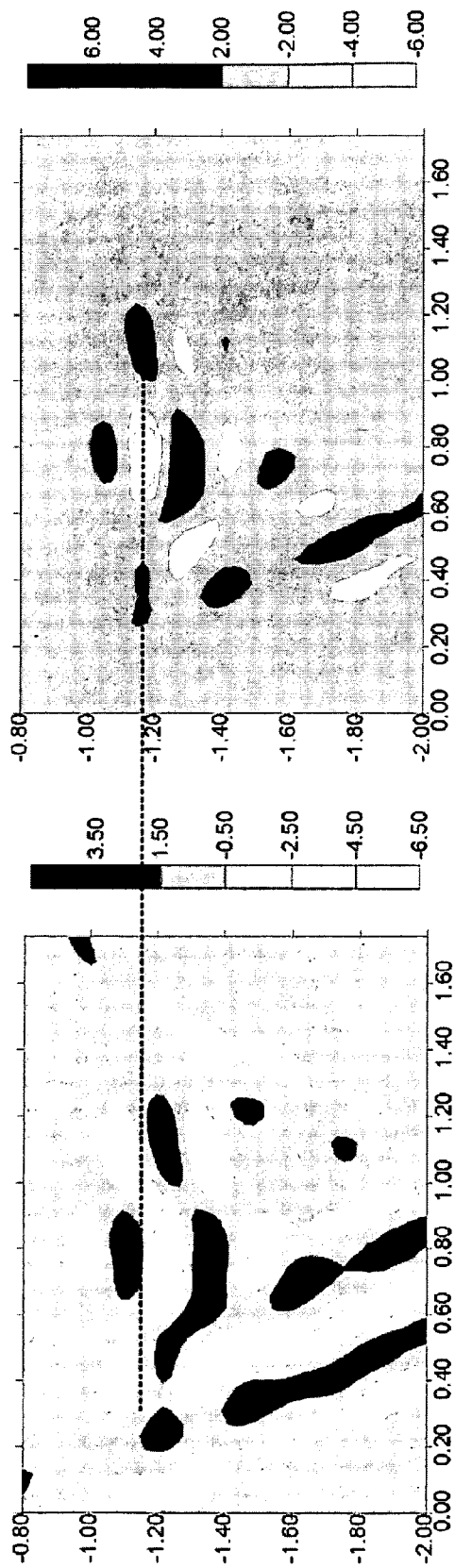
FIG. 19 shows vertical cross-sectional images of (a) $O_R$ and (b) $O_I$ reconstructed for the polystyrene disk (Target 1) without using analytic continuation.
Figure 20:
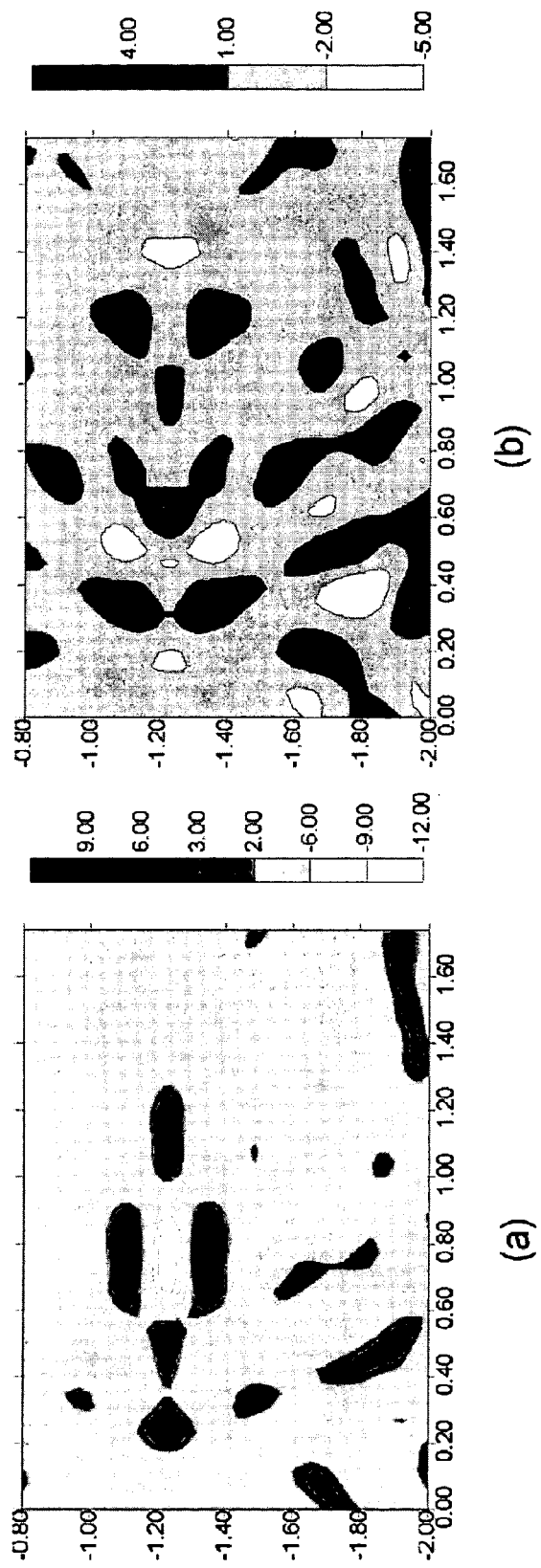
FIG. 20 shows vertical cross-sectional images of (a) $O_R$ and (b) $O_I$ reconstructed for the polystyrene disk (Target 1) using analytic continuation.

The polystyrene disk is a near-perfect dielectric and, as such, should exhibit little contrast with the dry sand background. There must be either a wave speed contrast or an attenuation contrast, or both, because otherwise this object would not produce the reflection evident in FIG. 13. Reconstructions of this feature without using analytic continuation are presented in FIG. 19. As with the other two objects, there is a noticeable depth offset between the speed- and attenuation-based images. For this target, both wave speed and attenuation exhibit a positive contrast with respect to the background. The companion reconstruction using analytic continuation is presented in FIG. 20. Here, there is a moderate increase in wave speed relative to the background (FIG. 20a) and, more significantly, the feature is completely absent in the attenuation image (FIG. 20b) with the appearance of only weak random noise.

Figure 21:
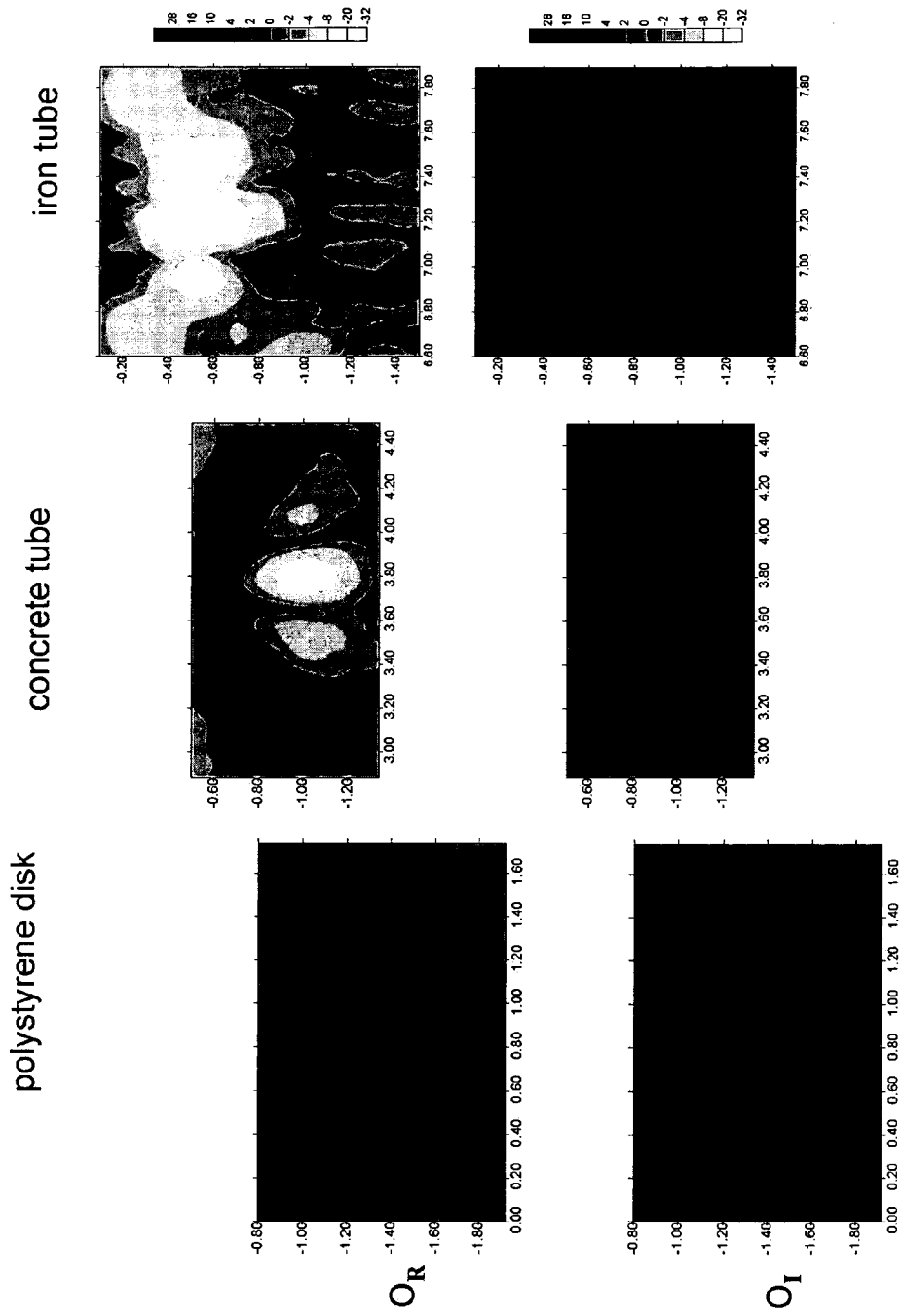
FIG. 21 shows vertical cross-sectional images of $O_R$ and $O_I$ reconstructed for the three targets using analytic continuation for the contrast and $|O|$ for the shape.

To compare the images reconstructed for all three targets using analytic continuation, FIG. 21 presents both wave speed and attenuation images at the same scale and with the same plotting contrast. For these images, the procedure used in FIG. 16 is again employed where |O| is used for the shape and the contrasts provided by $O_R$ and $O_I$ are used to scale the wave speed and attenuation images, respectively. In this form, there is the expected progression of a decrease in wave speed and an increase in attenuation from Target 1 (left) to Target 6 (right).

Synthetic Examples for Resource Exploration

There is large body of knowledge as to the structure of geologic formations that can yield oil or natural gas. However, the existence of these geologic structures, such as deep water channel sandstones, does not necessarily mean that oil or gas is present. From seismic data, the most reliable indicator of the presence of these resources is a local increase in attenuation. While it is possible to reliably reconstruct separate images of spatial variations in wave speed and attenuation from cross-borehole measurements, there currently exists no straightforward way to extract attenuation from reflection measurements. As noted previously, the only manifestation of attenuation is in a phase shift in the real acquired time series. Without a priori knowledge of the depth (travel time) to a reflecting feature, direct inspection cannot reveal the presence of attenuation.

To demonstrate the efficacy of separately imaging wave speed and attenuation from reflection measurements using analytic continuation, reconstructed images are presented for synthetic data sets. In the first example, the subsurface vertical cross-sectional structure is characterized by a circle having a radius of 10 units centered at a depth of 30 units, which is the mid-depth of a 30 unit thick horizontal layer. Using the definitions of $A_R$ and $A_I$ previously introduced for the wave speed and attenuation contrasts, respectively, the complex contrast of the circle is denoted by $A^c = A_R^c + iA_I^c$ and that for the layer is defined to be $A^l = A_R^l + iA_I^l$. In all simulations, 32 horizontal measurement (receiver) locations having a 2 unit spacing are used, reconstructions are based on 32 frequencies uniformly distributed over the interval [15.625, 500] Hz, and a background wave speed of 2500 units per second and vertical plane wave illumination, Eqs. (9) and (10), are used.

Figure 22:
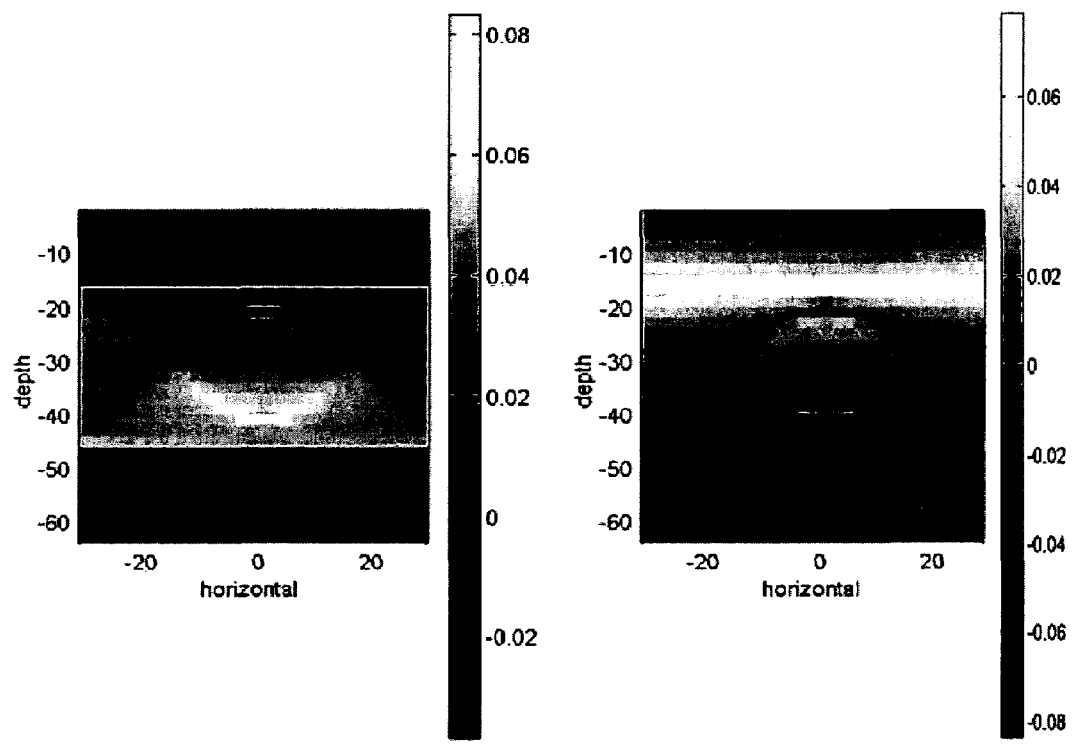
FIG. 22 shows a reconstructed image $O_R$ (left) and $O_I$ (right) obtained without analytic continuation for a attenuating circle embedded in a horizontal layer.
Figure 23:
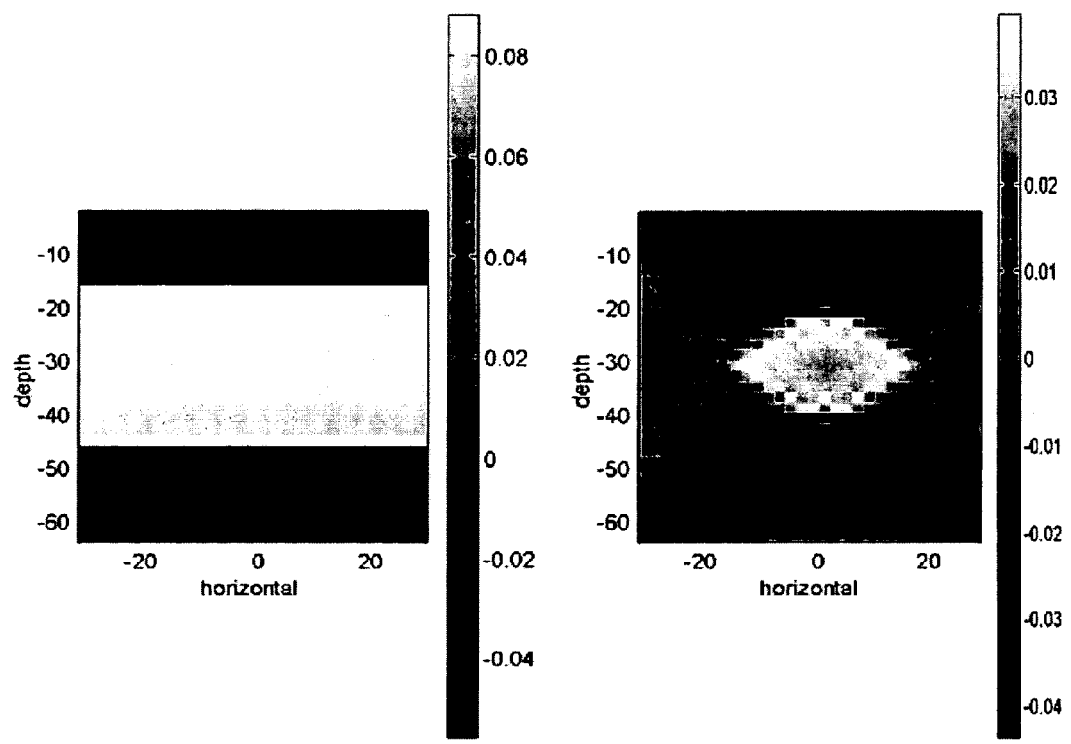
FIG. 23 shows a reconstructed image $O_R$ (left) and $O_I$ (right) obtained with analytic continuation for a attenuating circle embedded in a horizontal layer.
Figure 24:
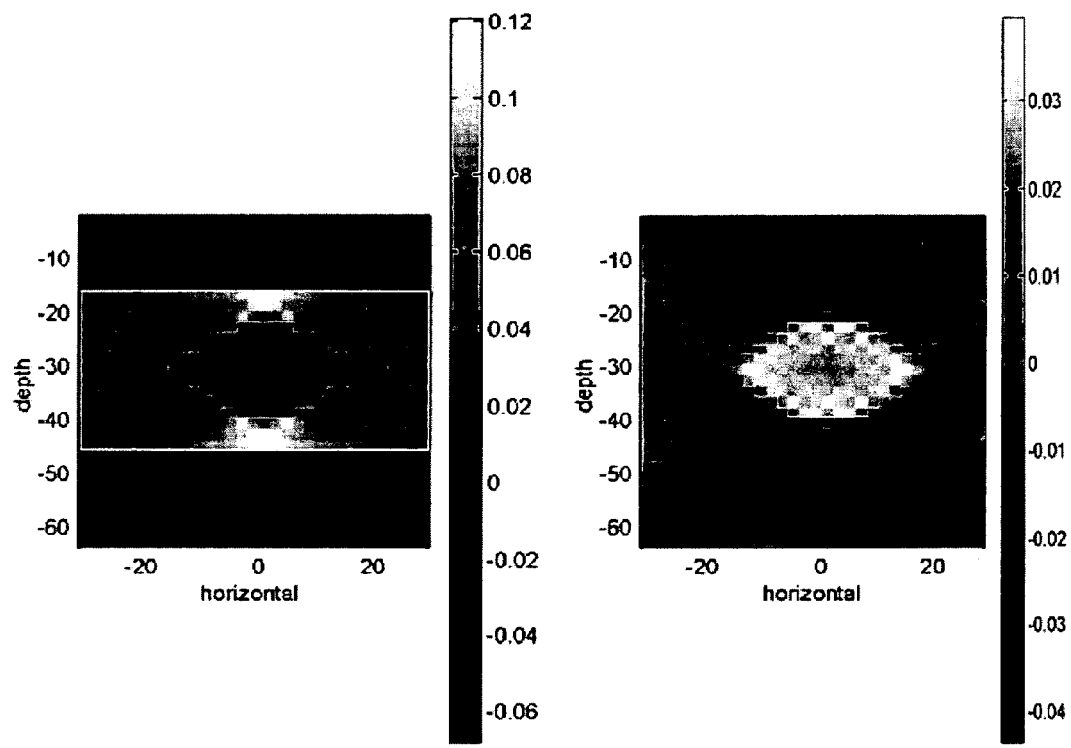
FIG. 24 shows a reconstructed image $O_R$ (left) and $O_I$ (right) obtained with analytic continuation for a circle with both wave speed and attenuation contrast embedded in a horizontal layer.

In the first simulation, the layer has only a contrast in wave speed, $A^l = 1 + 0i$, and the circle has no speed contrast but has an attenuation contrast relative to the layer, $A^c = 0 + 0.01i$. The reconstruction obtained without analytic continuation is shown in FIG. 22, and it is clear that both the layer and the circle improperly appear in the reconstruction of both $O_R$ and $O_I$ and that the upper and lower boundary of the circle in $O_R$ have opposite contrasts. Both of these artifacts are associated with the blending that is not properly represented in the image reconstruction procedure. FIG. 23 is the same reconstruction as given in FIG. 22 but with the application of analytic continuation. Here, the reconstruction properly represents the contrasts used in the simulation. The layer parameters are the same for the second simulation, and both a wave speed and an attenuation contrast, $A^c = -0.01 + 0.01i$, is specified for the circle. The reconstructed image should now reveal both the layer and the circle in the $O_R$ reconstruction and only the circle in the $O_I$ reconstruction. The result of the application of the analytic continuation to the imaging is shown in FIG. 24 and here all features are properly represented in the images.

Figure 25:
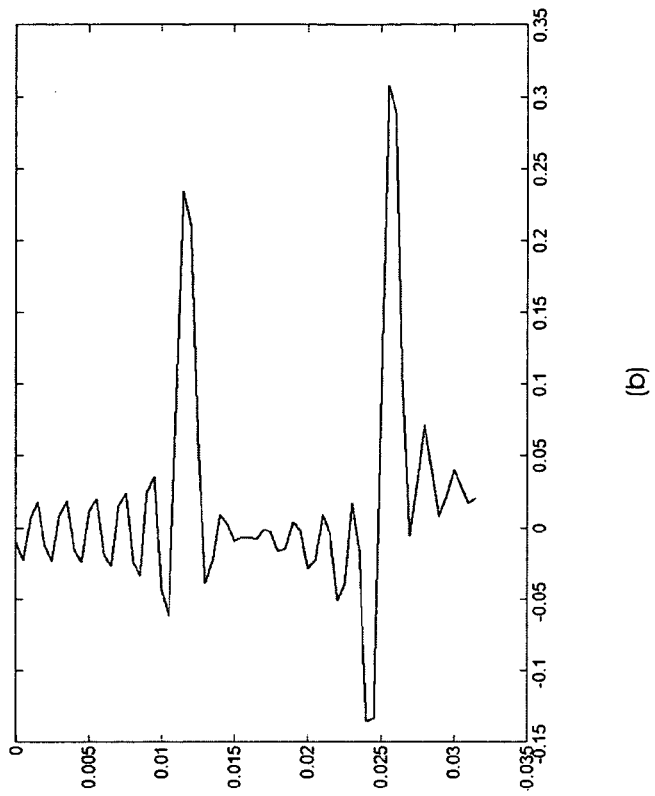
FIG. 25 is an example of (a) a vertical three-layer structure and (b) a reflection measurement trace for this configuration.
Figure 25:
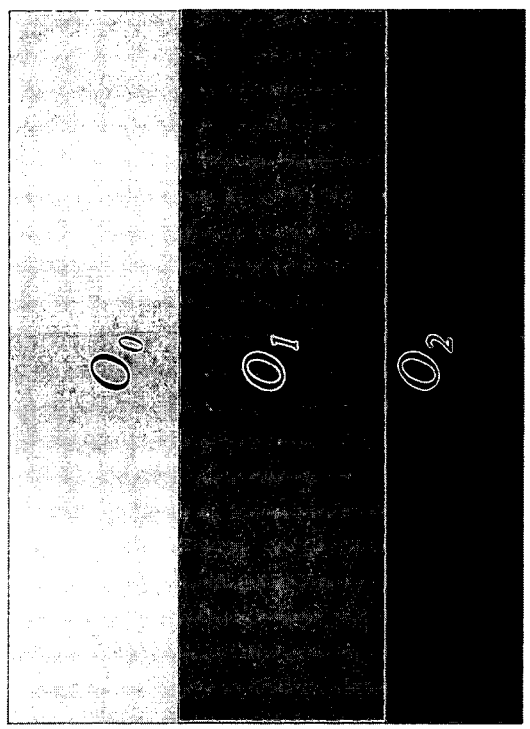
Figure 26:
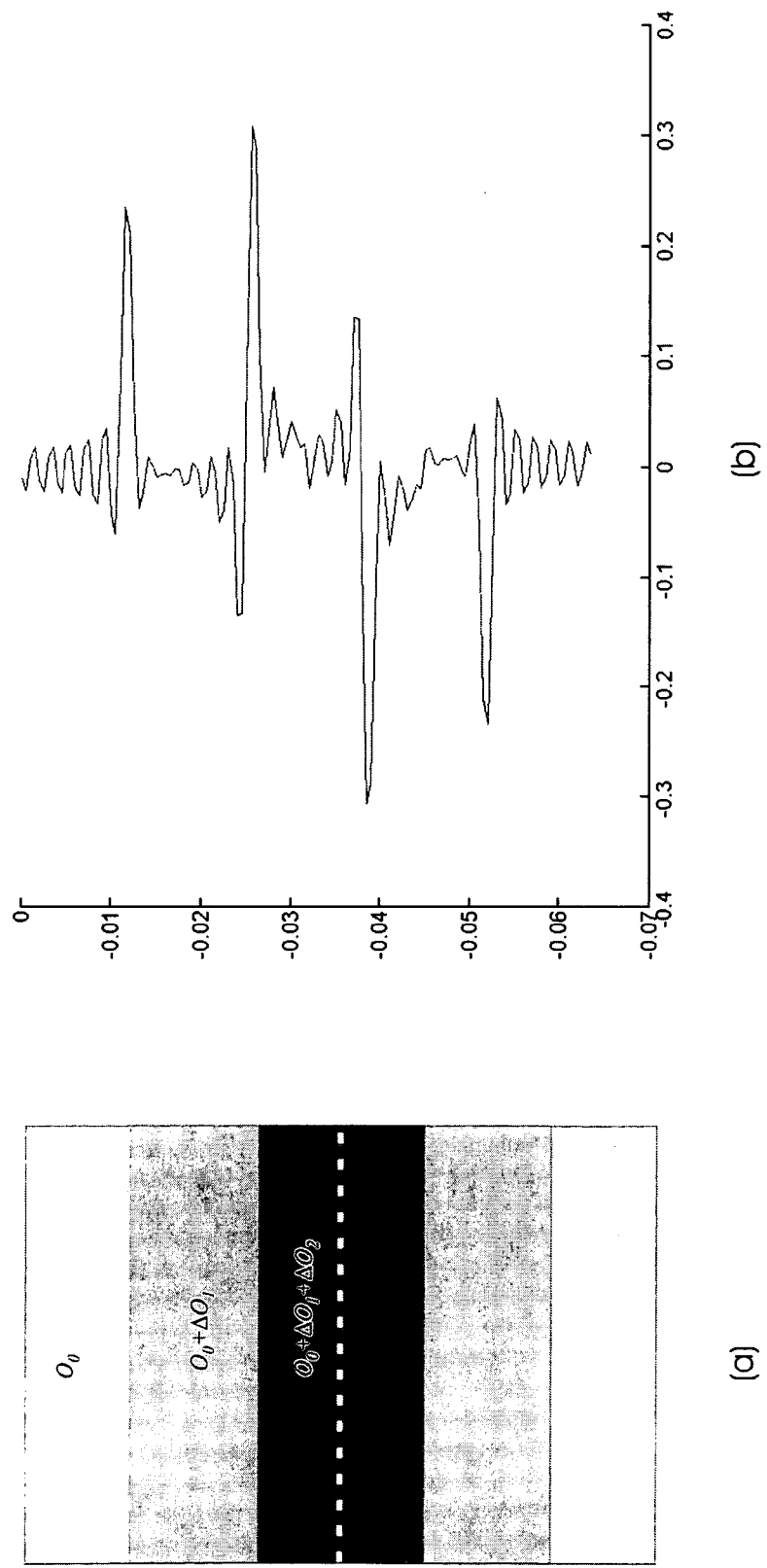
FIG. 26 is the mirrored version of (a) the layered structure and (b) data derived from the configuration and data shown in FIG. 25.

As previously noted, the application of the analytic continuation procedure requires two phase shifts: the first to move a feature to the origin and the second, applied after analytic continuation, to reposition the imaged feature to its proper location. For the processing of ground penetrating radar data, this shifting was applied separately for each imaged object and required that the manifestation of each feature in the acquired data be isolated. A difficulty in phase shifting can occur when the imaged structure is a sequence of layers such as that shown in FIG. 25a. Here, there are two horizontal interfaces separating three layers defined by complex object functions $O_0$, $O_1$, and $O_2$. The transitions between the upper and lower boundaries of the middle layer are transitions between $O_0/O_1$ and $O_1/O_2$, respectively. The synthetic plane wave reflection data for this layered geometry is shown in FIG. 25b. It might seem possible to isolate the reflections from this middle layer in the data by considering only an appropriately selected time window. However, this is not the case because the upper reflection is a manifestation of the contrast between the middle and upper layer and the lower reflection is a manifestation of the contrast between the middle and lower layers. Unlike isolated objects, the manifestation of a single layer in reflection data cannot be isolated from those that occur above and below, which presents a problem in implementing the phase shifting required for analytic continuation. This difficulty can be overcome by considering the layer geometry as a linear superposition of multiple layers all having a common mid-depth. It should be noted that such a superposition is entirely consistent with linearized scattering theory. The effect is the vertical mirroring of the layer structure as shown in FIG. 26a. Here, it is assumed that a homogeneous background exists and is characterized by an object function $O_0$. Superimposed on this background is, at first, an incremental change into the middle layer $O_1 = O_0 + \Delta O_1$ with a second incremental change into the deeper layer $O_2 = O_1 + \Delta O_2 = O_0 + \Delta O_1 + \Delta O_2$. In order to properly image this modified layered structure, it is necessary to have reflection information from the four interfaces shown in FIG. 26a. This can be accomplished by a simple mirroring of the data. FIG. 26b is the mirrored version of the data shown in FIG. 25b that is consistent with all the interfaces evident in FIG. 26a. The required phase shift can be based on either the common mid-depth of all layers shown in FIG. 26a (the dashed line) or, equivalently, the maximum measurement time (FIG. 25b).

Figure 27:
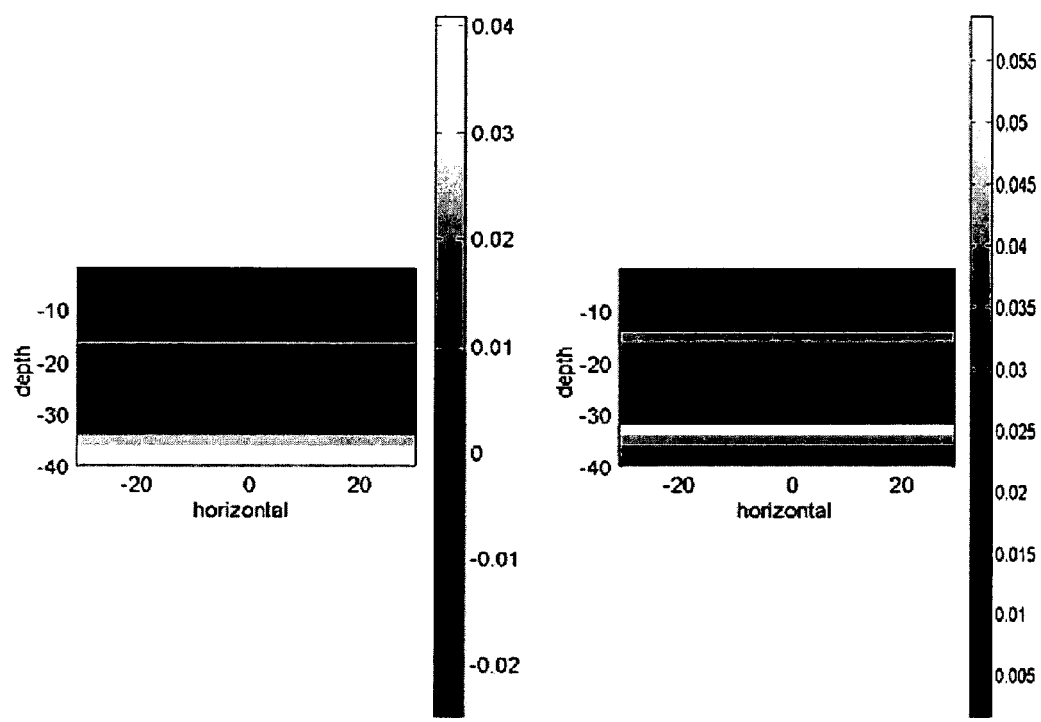
Figure 28:
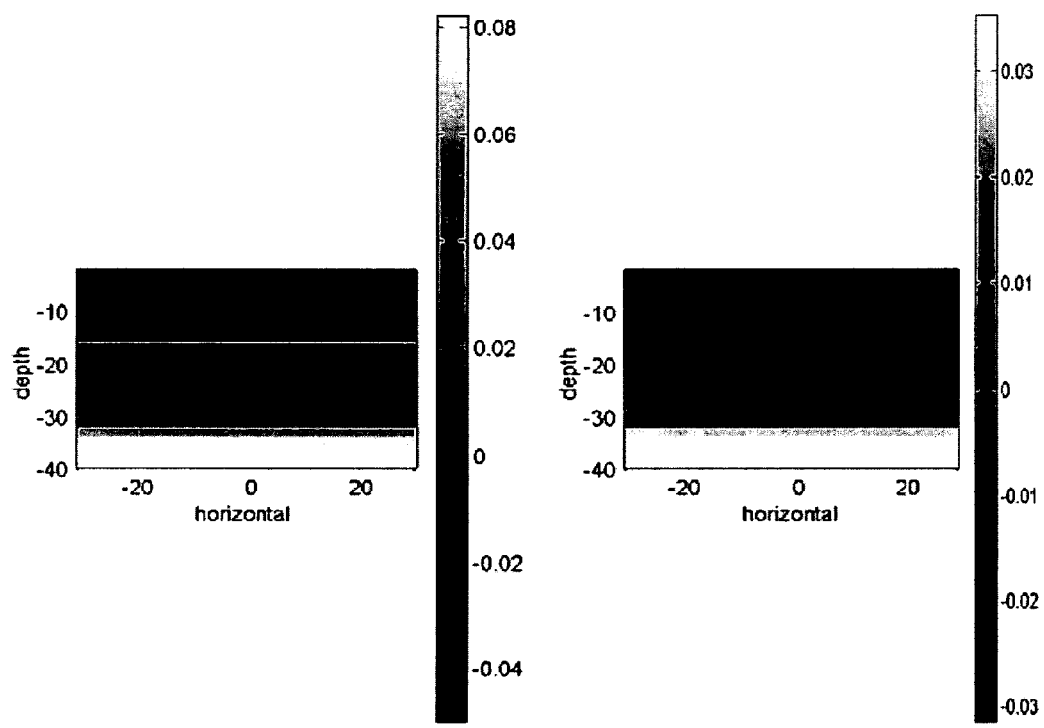
Figure 29:
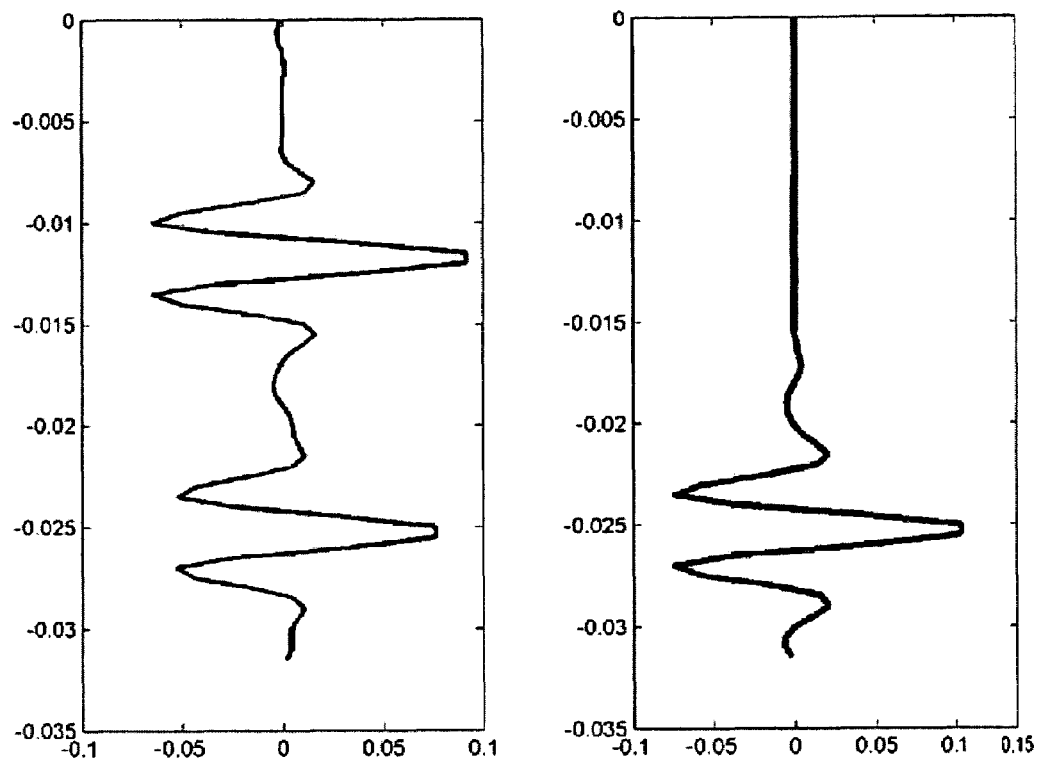

Images have been reconstructed assuming that $O_0 = 0$, $O_1 = 1 + 0i$, and $O_2 = O_1 + 1 + 1i$. For these parameters, there is change in wave speed (the real part of O) across all interfaces but only the lower layer of FIG. 25a has attenuation. The process is to use the mirrored version (FIG. 26b) of the actual data (FIG. 25b) to reconstruct images without analytic continuation (FIG. 27) and with analytic continuation (FIG. 28). As is readily apparent in FIG. 27, the image without analytic continuation reveals both wave speed and attenuation contrasts across both interfaces, a result that is clearly incorrect. The image derived using analytic continuation (FIG. 28) properly demonstrates a wave speed contrast across both interfaces but an attenuation contrast across only one interface. For completeness, the data reconstituted after analytic continuation is provided in FIG. 29, and again the proper contrasts are evident. There is a wave speed reflection from both interfaces, but an attenuation reflection from only the deeper interface.

CONCLUSION

As discussed above, an extension of the above results to multiple dimensions is straightforward. In the one-dimensional example, it was assumed that some function f (z) is Fourier transformed with respect to z to yield the transformed function $F(\kappa)$. It was further assumed that $F(\kappa)$ was known only for $\kappa > 0$. To analytically continue $F(\kappa)$ into $\kappa < 0$, taking f to be an even function, the formula $F(-\kappa) = F(\kappa)$ is used. For higher dimensionality (three-dimensional, for example), K is replaced by a three-dimensional vector $K = (K_x, K_y, K_z)$ and the analytic continuation becomes $F(K) = F(K_x, K_y, K_z) = F(-K) = F(-K_x, -K_y, -K_z)$.

Figure 30:
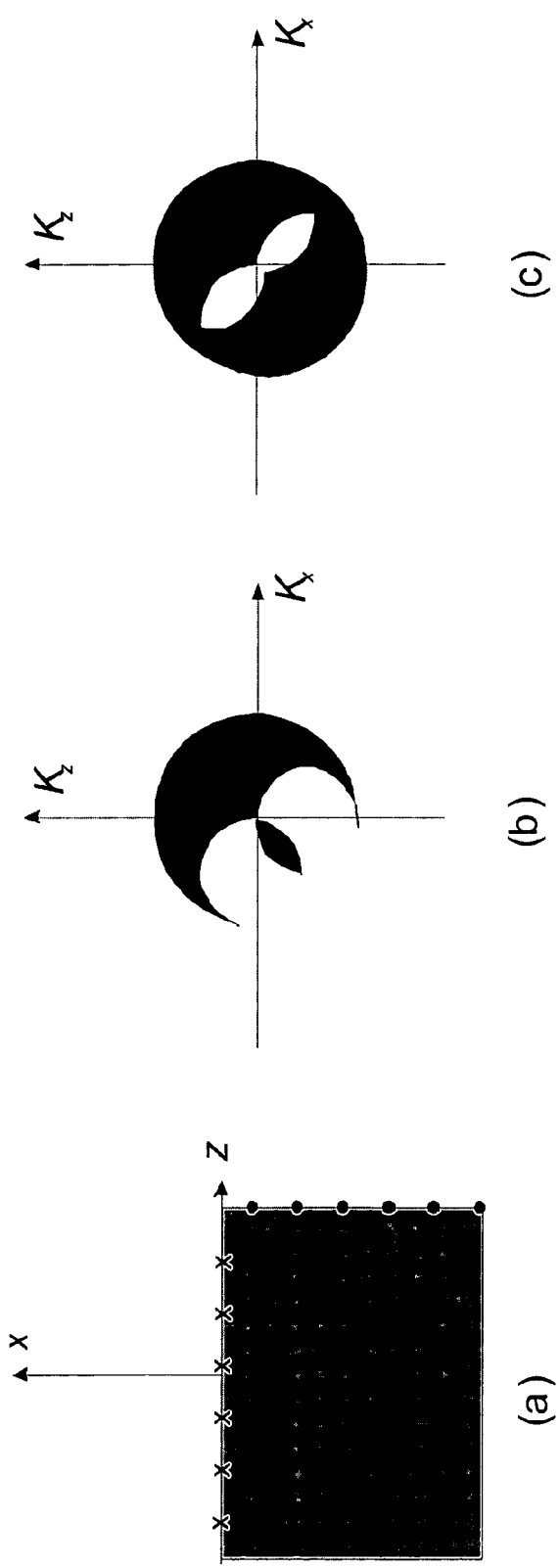
FIG. 30 shows (a) a two-dimensional example for a line of sources on the ground surface and a line of receivers in a vertical borehole, (b) K-space coverage, and (c) analytically continued K-space coverage.

A two dimensional example is given in FIG. 30 for a line of sources on the ground surface and a line of receivers in a vertical borehole (FIG. 30a). The K-space coverage for this measurement geometry is given in FIG. 30b. Analytical continuation of this coverage using $F(-K_x, -K_z) = F(K_x, K_z)$ gives the desired coverage that is symmetric with respect to the origin (FIG. 30c).

Consider an isolated object such as a buried pipe or a tumor where, for simplicity, only two dimensions (x, y) are considered. Let this object be defined by the function f(x, y), and let this object be centered at $(x=0, y=y_0)$. Define the Fourier transform of this function when centered at $(x=0, y=0)$ to be $F(K_x, K_y)$. By the shift rule for Fourier transforms, the Fourier transform of the object when centered at $(x=0, y=y_0)$ is $F(K_x, K_y) \exp(-i K_y y_0)$. Assuming that F is known for $K_y > 0$, analytically continuing this function into $K_y < 0$ will alter the term $\exp(-i K_y y_0)$ such that the object appears at $-y_0$ for $K_y < 0$. For isolated objects where data associated with an identified object can be isolated, this segment of the data may be phase shifted to the origin, an analytic continuation applied, and then another phase shift may be used to restore it to the proper depth.

Figure 31:
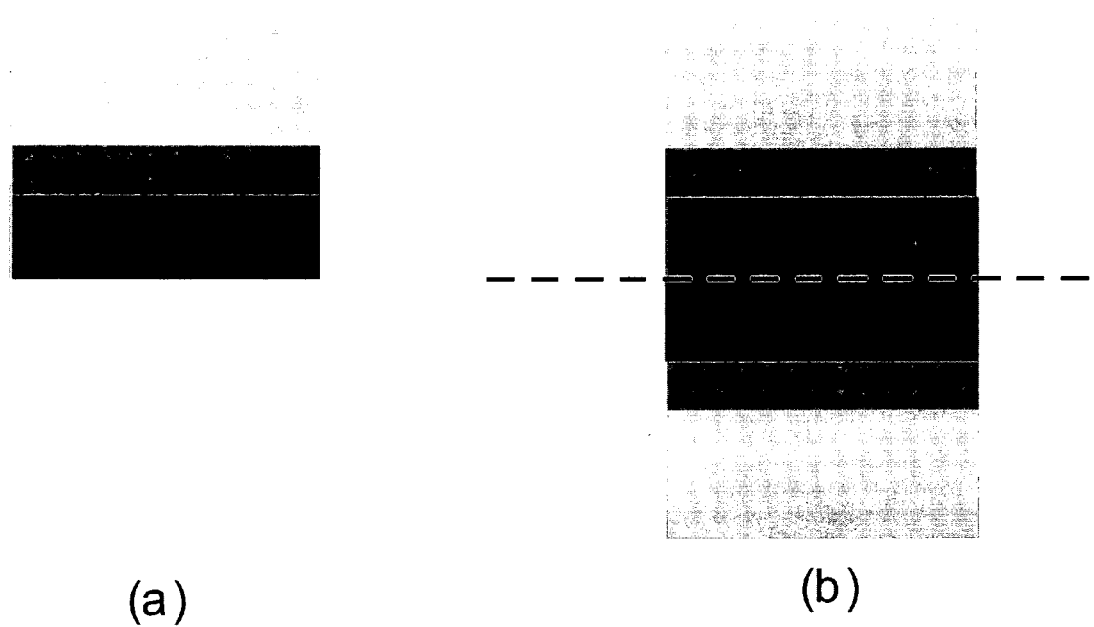
FIG. 31 shows a layered example in which mirroring may be applied in one dimension to permit simultaneous phase shifting of all layers.

Finally, with regard to phase shifting and mirroring, the phase shifting procedure discussed above requires that individual objects be isolated in the data and processed independently, which is not always possible. As an example, consider the layered structure shown in FIG. 31a. The bottom of one layer shares a boundary with the top of the deeper layer making it impossible to isolate each layer. Layers are commonly encountered in geophysical exploration using seismic reflection where measurements are made on the ground surface, as was discussed in an earlier example. In these measurements, depth information is restricted by the total time over which measurements are recorded, where information at greater depths comes from longer recording times. Thus, the bottom of FIG. 31a does not necessarily indicate the bottom of the layer, but rather the termination of information. As shown in FIG. 31a, layers are stacked vertically; however, they can also be treated as superimposed one on top of the other. By mirroring the data, the layer geometry is mirrored as shown in FIG. 31b. The result of this mirroring procedure is that all layers have a common mid-depth, as denoted by the dashed line and, for this reason, all layers can be simultaneously phase shifted, thereby eliminating the problem of isolating individual layers.

Figure 32:
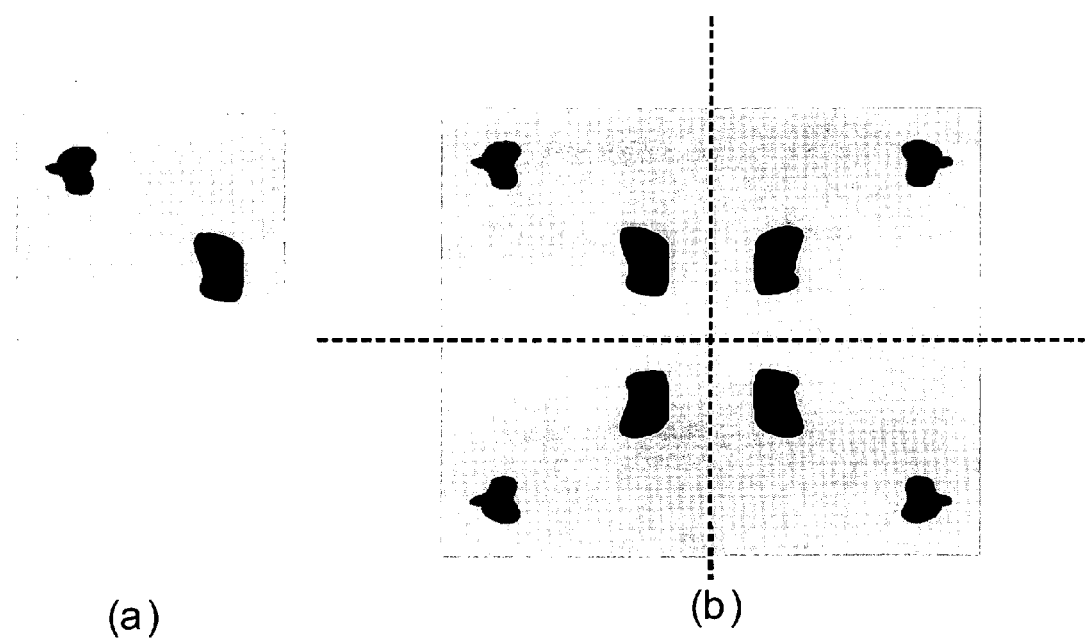
FIG. 32 shows how mirroring may be applied in two dimensions with two isolated objects.
Figure 33:
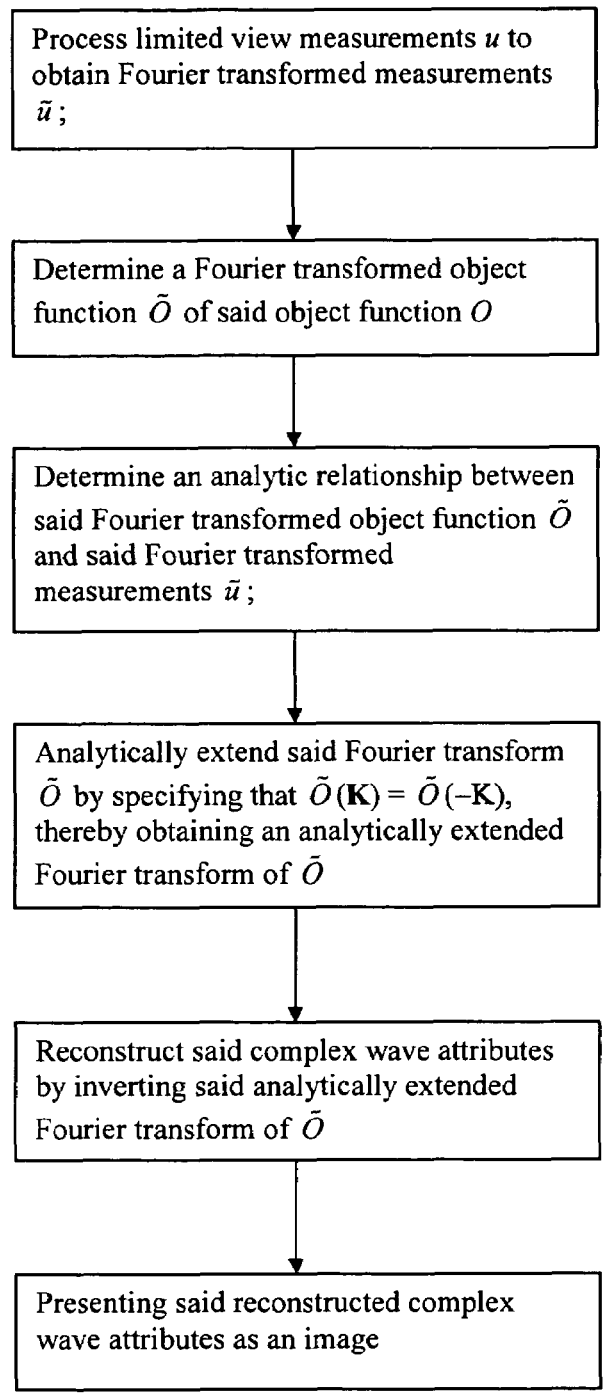
FIG. 33 shows a flow chart of the steps in an embodiment of the claimed invention.
Figure 34:
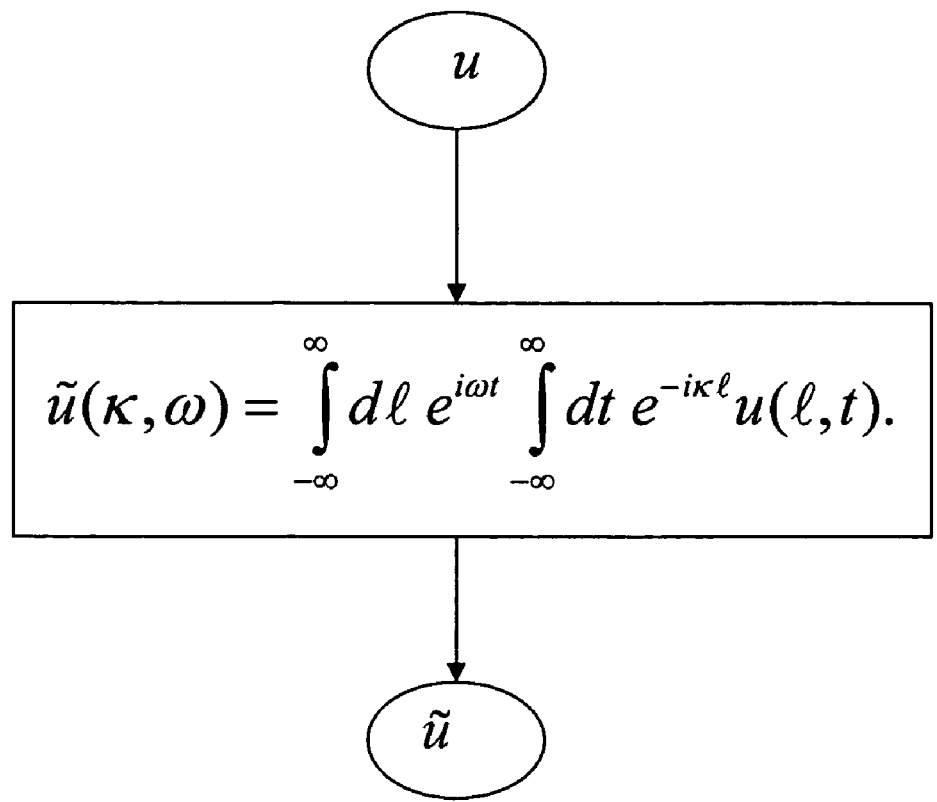
FIG. 34 shows a flow chart of the processing step of an embodiment of the claimed invention.

The previous example requires mirroring in only one dimension. Mirroring can be applied in two, or more, dimensions as well. For example, consider two isolated objects (in two dimensions) as shown in FIG. 32a. Mirroring can be applied both vertically (as in FIG. 31b) and horizontally as shown in FIG. 32b. Here, the center-point (the point to which phase shifting is applied) is the intersection of the dashed lines. This multidimensional mirroring can also be applied to layers that are not horizontal.

If it were possible to image from measurements taken on an arbitrary shaped surface, then it would be straightforward to apply the analytic continuation methods disclosed herein. Specifically, "padding" could be applied to the space between the actual imaged volume and a rectangular shape (or similar easily Fourier transformed shape) with zeroes or some constant background value. The object function could then be Fourier transformed and analytic continuation could be applied.

The present invention, therefore, is well adapted to carry out the objects and obtain the ends and advantages mentioned above, as well as others inherent herein. All presently preferred embodiments of the invention have been given for the purposes of disclosure. Where in the foregoing description reference has been made to elements having known equivalents, then such equivalents are included as if they were individually set forth. Although the invention has been described by way of example and with reference to particular embodiments, it is not intended that this invention be limited to those particular examples and embodiments. It is to be understood that numerous modifications and/or improvements in detail of construction may be made that will readily suggest themselves to those skilled in the art and that are encompassed within the spirit of the invention and the scope of the appended claims.

The invention claimed is:

1. A method for reconstructing complex wave attributes described by an object function O from limited view measurements u of a measurement surface r with associated wavevector K, said method comprising the steps of:
processing said limited view measurements u to obtain Fourier transformed measurements $\tilde{u}$;
determining a Fourier transformed object function $\tilde{O}$ of said object function $\tilde{O}$;
determining an analytic relationship between said Fourier transformed object function $\tilde{O}$ and said Fourier transformed measurements $\tilde{u}$;
analytically extending said Fourier transform $\tilde{O}$ by specifying that $\tilde{O}(K)=\tilde{O}(-K)$, thereby obtaining an analytically extended Fourier transform of $\tilde{O}$;
reconstructing said complex wave attributes by inverting said analytically extended Fourier transform of $\tilde{O}$; and,
presenting said reconstructed complex wave attributes as an image.

2. The method of claim 1 wherein said complex wave attributes are wave speed and attenuation.

3. The method of claim 1 wherein said complex wave attributes are dielectric and electric conductivity.

4. The method of claim 1 wherein said complex wave attributes are acoustic wave speed density and compressibility.

5. The method of claim 1 wherein said object function is one-dimensional.

6. The method of claim 1 wherein said object function is two-dimensional.

7. The method of claim 1 wherein said object function is three-dimensional.

8. The method of claim 1 wherein said measurement surface r comprises a ring.

9. The method of claim 1 wherein said measurement surface r comprises a sphere.

10. The method of claim 1 wherein said measurement surface r comprises a cylinder.

11. The method of claim 1 wherein said measurement surface r comprises a plurality of parallel lines.

12. The method of claim 1 wherein said measurement surface r comprises a plurality of perpendicular lines.

13. The method of claim 1 wherein said measurement surface r comprises a line and a curved surface.

14. The method of claim 1 wherein said limited view measurements are time domain measurements.

15. The method of claim 1 wherein said limited view measurements are frequency domain measurements.

16. A method for reconstructing complex wave attributes described by an object function O from limited view measurements u of an object with associated wavevector K, said method comprising the steps of:
processing said measurements u to obtain Fourier transformed measurements $\tilde{u}$; determining a midpoint of said object;
creating shifted Fourier transformed measurements $\tilde{u}_R$ by shifting said Fourier transformed measurements $\tilde{u}$ so that said midpoint is located at the origin;
determining an analytic relationship between said object function O and said shifted Fourier transformed measurements $\tilde{u}_R$;
determining the Fourier transform $\tilde{O}$ of said object function O from said Fourier transformed measurements $\tilde{u}_R$ using said analytic relationship;
analytically extending said Fourier transform $\tilde{O}$ by specifying that $\tilde{O}(K)=\tilde{O}(-K)$, thereby obtaining an analytically extended Fourier transform of $\tilde{O}$;
determining shifted complex wave attributes by inverting said analytically extended Fourier transform of $\tilde{O}$;
reconstructing said complex wave attributes by shifting said shifted complex wave attributes back to said midpoint; and,
presenting said reconstructed complex wave attributes as an image.

17. The method of claim 16 wherein said step of determining a midpoint comprises the steps of:
determining the complex contrast of said object;
determining the magnitude of said complex contrast; and, choosing said midpoint to be the center location of said complex contrast.

18. The method of claim 16 wherein said step of determining a midpoint comprises the steps of:

determining the complex contrast of said object;

determining the magnitude of said complex contrast; and, choosing said midpoint to be the mid-depth of said complex contrast.

19. The method of claim 16 wherein said midpoint is a spatial component and said step of determining a midpoint comprises choosing said midpoint to be the depth achieved at the maximum measured travel time.

20. The method of claim 16 wherein said midpoint is a temporal component and said step of determining a midpoint comprises choosing said midpoint to be the maximum measured travel time.

* * * * *